US010729856B1

(12) United States Patent
Nock et al.

(10) Patent No.: US 10,729,856 B1
(45) Date of Patent: Aug. 4, 2020

(54) GUIDE AND FILTER FOR BIOPSY DEVICE

(71) Applicant: Devicor Medical Products, Inc., Cincinnati, OH (US)

(72) Inventors: Andrew P. Nock, Dayton, OH (US); Robert M. Householder, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 85 days.

(21) Appl. No.: 15/664,461

(22) Filed: Jul. 31, 2017

Related U.S. Application Data

(60) Provisional application No. 62/368,684, filed on Jul. 29, 2016.

(51) Int. Cl.
| | |
|---|---|
| *A61M 5/31* | (2006.01) |
| *A61B 10/02* | (2006.01) |
| *A61B 10/00* | (2006.01) |
| *A61M 39/22* | (2006.01) |
| *A61B 17/34* | (2006.01) |
| *A61M 5/158* | (2006.01) |
| *A61M 25/00* | (2006.01) |

(52) U.S. Cl.
CPC ....... *A61M 5/3145* (2013.01); *A61B 10/0096* (2013.01); *A61B 10/0266* (2013.01); *A61B 10/02* (2013.01); *A61B 10/0283* (2013.01); *A61B 17/3417* (2013.01); *A61B 2010/0208* (2013.01); *A61M 5/1582* (2013.01); *A61M 25/0026* (2013.01); *A61M 2039/229* (2013.01)

(58) Field of Classification Search
CPC . A61B 10/02; A61B 10/0233; A61B 10/0283; A61B 2010/0208; A61B 2010/0225; A61B 10/0266; A61B 10/0096; A61B 17/3417; A61M 1/00; A61M 25/0026; A61M 5/1582
See application file for complete search history.

(56) References Cited

U.S. PATENT DOCUMENTS

| | | | |
|---|---|---|---|
| 5,526,822 A | 6/1996 | Burbank et al. |
| 5,928,164 A | 7/1999 | Burbank et al. |
| 6,017,316 A | 1/2000 | Ritchart et al. |
| 6,086,544 A | 7/2000 | Hibner et al. |

(Continued)

OTHER PUBLICATIONS

U.S. Appl. No. 62/368,684, filed Jul. 29, 2016.

*Primary Examiner* — Christian Jang
*Assistant Examiner* — Karen E Toth
(74) *Attorney, Agent, or Firm* — Frost Brown Todd LLC

(57) ABSTRACT

An apparatus includes a needle, a cutter, a medication fluid path, and a filter assembly. The needle defines a tissue receiving feature. The cutter is movable relative to the needle to sever tissue protruding into the tissue receiving feature. The medication fluid path includes a first portion and a second portion. The first portion is configured to couple with a source of medication fluid. The tissue receiving feature is in fluid communication with the medication fluid path such that the first portion is upstream of the tissue receiving feature. The filter assembly is located in the second portion of the medication fluid path. The filter assembly is configured to permit air to pass through the filter assembly. The filter assembly is further configured to prevent medication fluid from passing through the filter assembly.

19 Claims, 26 Drawing Sheets

(56) References Cited

U.S. PATENT DOCUMENTS

| | | | |
|---|---|---|---|
| 6,162,187 A | 12/2000 | Buzzard et al. | |
| 6,432,065 B1 | 8/2002 | Burdorff et al. | |
| 6,485,436 B1* | 11/2002 | Truckai | A61B 10/0275 600/564 |
| 6,626,849 B2 | 9/2003 | Huitema et al. | |
| 6,752,768 B2 | 6/2004 | Burdorff et al. | |
| 7,442,171 B2 | 10/2008 | Stephens et al. | |
| 7,507,210 B2 | 3/2009 | Hibner et al. | |
| 7,648,466 B2 | 1/2010 | Stephens et al. | |
| 7,831,290 B2 | 11/2010 | Hughes et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,918,803 B2 | 4/2011 | Ritchart et al. | |
| 7,938,786 B2 | 5/2011 | Ritchie et al. | |
| 8,083,687 B2 | 12/2011 | Parihar | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,454,531 B2 | 6/2013 | Speeg et al. | |
| 8,568,333 B2 | 10/2013 | Hibner et al. | |
| 8,622,924 B2 | 1/2014 | Speeg et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,095,326 B2 | 8/2015 | Ritchie et al. | |
| 9,326,755 B2 | 5/2016 | Fiebig et al. | |
| 9,345,457 B2 | 5/2016 | Speeg et al. | |
| 9,486,186 B2 | 11/2016 | Fiebig et al. | |
| 9,724,076 B2 | 8/2017 | Fiebig et al. | |
| 9,955,955 B2 | 5/2018 | Fiebig et al. | |
| 2006/0074345 A1 | 4/2006 | Hibner | |
| 2007/0032740 A1* | 2/2007 | Quick | A61B 10/0275 600/566 |
| 2007/0083187 A1* | 4/2007 | Eversull | A61M 25/10 604/508 |
| 2009/0131821 A1 | 5/2009 | Speeg et al. | |
| 2009/0216151 A1* | 8/2009 | Speeg | A61B 10/0275 600/567 |
| 2010/0152610 A1 | 6/2010 | Parihar et al. | |
| 2010/0160819 A1 | 6/2010 | Parihar et al. | |
| 2011/0105945 A1* | 5/2011 | Videbaek | A61B 10/0275 600/567 |
| 2013/0053724 A1* | 2/2013 | Fiebig | A61B 10/0266 600/567 |
| 2013/0123663 A1* | 5/2013 | Hibner | A61B 10/0275 600/566 |
| 2013/0324882 A1 | 12/2013 | Mescher | |
| 2014/0039343 A1 | 2/2014 | Mescher et al. | |
| 2014/0276209 A1* | 9/2014 | Hibner | A61B 10/0275 600/567 |
| 2017/0311935 A1* | 11/2017 | Choung | A61B 10/0266 |

* cited by examiner

GUIDE AND FILTER FOR BIOPSY DEVICE

PRIORITY

This application claims priority to U.S. Provisional Pat. App. No. 62/368,684, entitled "Modified MRI Breast Biopsy Equipment," filed Jul. 29, 2016, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 21, 2012; U.S. Pat. No. 8,801,742, entitled "Needle Assembly and Blade Assembly for Biopsy Device," issued Aug. 12, 2014; U.S. Pat. No. 8,938,285, entitled "Access Chamber and Markers for Biopsy Device," issued Jan. 20, 2015; and U.S. Pat. No. 8,858,465, entitled "Biopsy Device with Motorized Needle Firing," issued Oct. 14, 2014. The disclosure of each of the above-cited U.S. Patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006 (abandoned—Jun. 10, 2009); U.S. Pat. No. 9,095,326, entitled "Biopsy System with Vacuum Control Module," issued Aug. 4, 2015; U.S. Pat. No. 9,345,457, entitled "Presentation of Biopsy Sample by Biopsy Device," issued May 24, 2016); U.S. Pat. No. 8,118,755, entitled "Biopsy Sample Storage," issued Feb. 21, 2012; U.S. Pat. Pub. No. 2009/0131821, entitled "Graphical User Interface For Biopsy System Control Module," published May 21, 2009 (abandoned—Apr. 12, 2011); U.S. Pat. No. 8,454,531, entitled "Icon-Based User Interface on Biopsy System Control Module," issued Jun. 4, 2013; U.S. Pat. No. 8,241,226, entitled "Biopsy Device with Rotatable Tissue Sample Holder," issued Aug. 14, 2012; U.S. Pat. Pub. No. 2010/0152610, entitled "Hand Actuated Tetherless Biopsy Device with Pistol Grip," published Jun. 17, 2010 (abandoned—Feb. 23, 2011); U.S. Pat. Pub. No. 2010/0160819, entitled "Biopsy Device with Central Thumbwheel," published Jun. 24, 2010 (abandoned—Oct. 5, 2012); U.S. Pat. No. 8,702,623, entitled "Biopsy Device with Discrete Tissue Chambers," issued Apr. 22, 2014; U.S. Pat. No. 8,206,316, entitled "Tetherless Biopsy Device with Reusable Portion," issued Jun. 26, 2012; U.S. Pat. No. 8,764,680, entitled "Handheld Biopsy Device with Needle Firing," issued Jul. 1, 2014; U.S. Pat. No. 9,326,755, entitled "Biopsy Device Tissue Sample Holder with Bulk Chamber and Pathology Chamber," issued May 3, 2016; U.S. Pat. No. 9,486,186, entitled "Biopsy Device With Slide-In Probe," issued Nov. 8, 2016; and U.S. Pat. Pub. No. 2013/0324882, entitled "Control for Biopsy Device," published Dec. 5, 2013 (abandoned—Apr. 27, 2016). The disclosure of each of the above-cited U.S. Patents and U.S. Patent Application Publications is incorporated by reference herein.

In U.S. Pat. No. 7,831,290, entitled "MRI Biopsy Device Localization Fixture" issued Nov. 9, 2010, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a cannula/sleeve to a biopsy site of suspicious tissues or lesions. Another merely illustrative localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
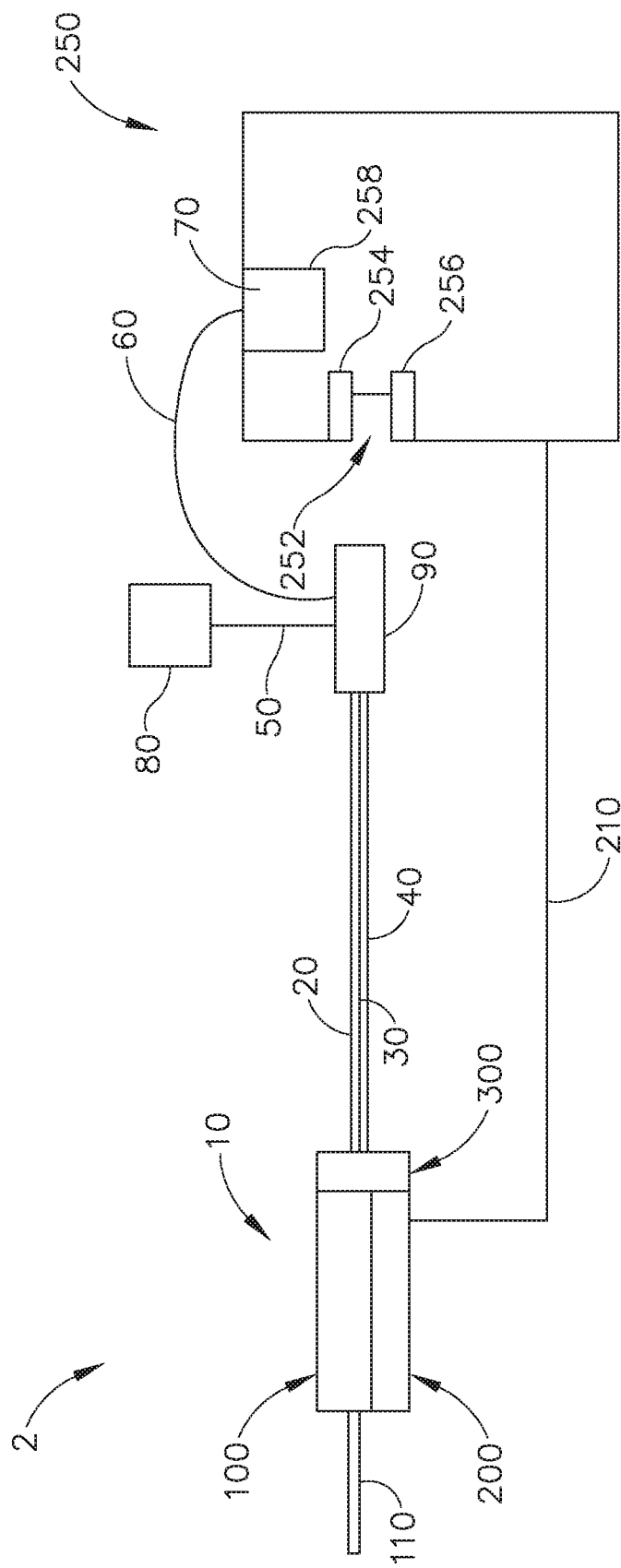
FIG. 1 depicts a schematic view of an exemplary biopsy system.
Figure 2:
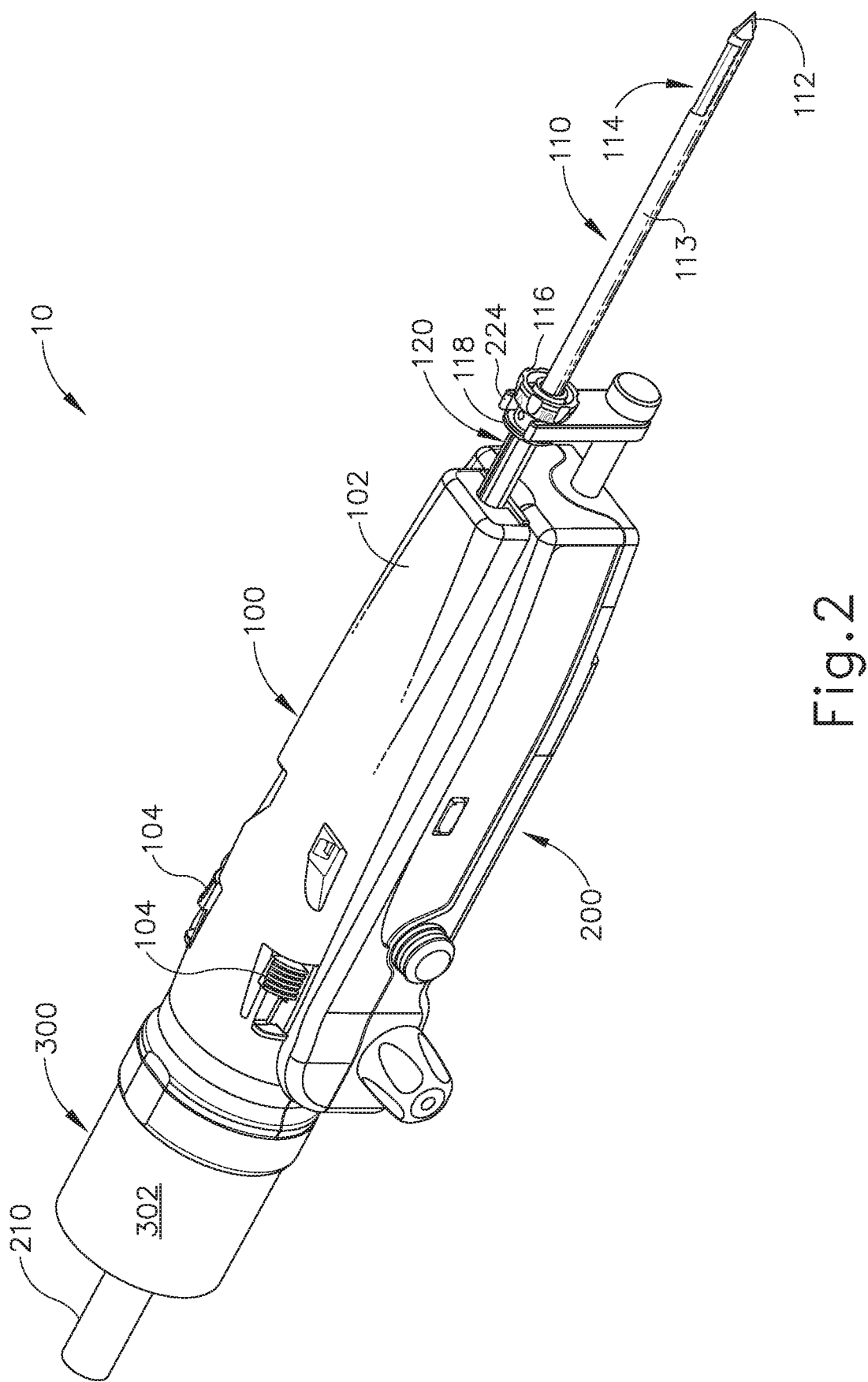
FIG. 2 depicts a perspective view of an exemplary biopsy device of the biopsy system of FIG. 1, including an exemplary probe coupled with an exemplary holster.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Biopsy System

FIG. 1 depicts an exemplary biopsy system (2) comprising a biopsy device (10) and a vacuum control module (250). By way of example only, at least some components of biopsy system (2) may be configured and/or operable in accordance with at least some of the teachings of U.S. Pub. No. 2014/0039343, entitled "Biopsy System," published Feb. 6, 2014, the disclosure of which is incorporated by reference herein. Biopsy device (10) of this example comprises a probe (100) and a holster (200). A needle (110) extends distally from probe (100), and is inserted into a patient's tissue to obtain tissue samples as will be described in greater detail below. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (200). In the present example, holster (200) includes a set of prongs (208) that are received by the chassis (106) of probe (100) to releasably secure probe (100) to holster (200). In particular, probe (100) is first positioned on top of holster (200), just proximal to its final position relative to holster (200); then probe (100) is slid distally to fully engage prongs (208). Probe (100) also includes a set of resilient tabs (104) that may be pressed inwardly to disengage prongs (208), such that a user may simultaneously depress both tabs (104) then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Figure 4:
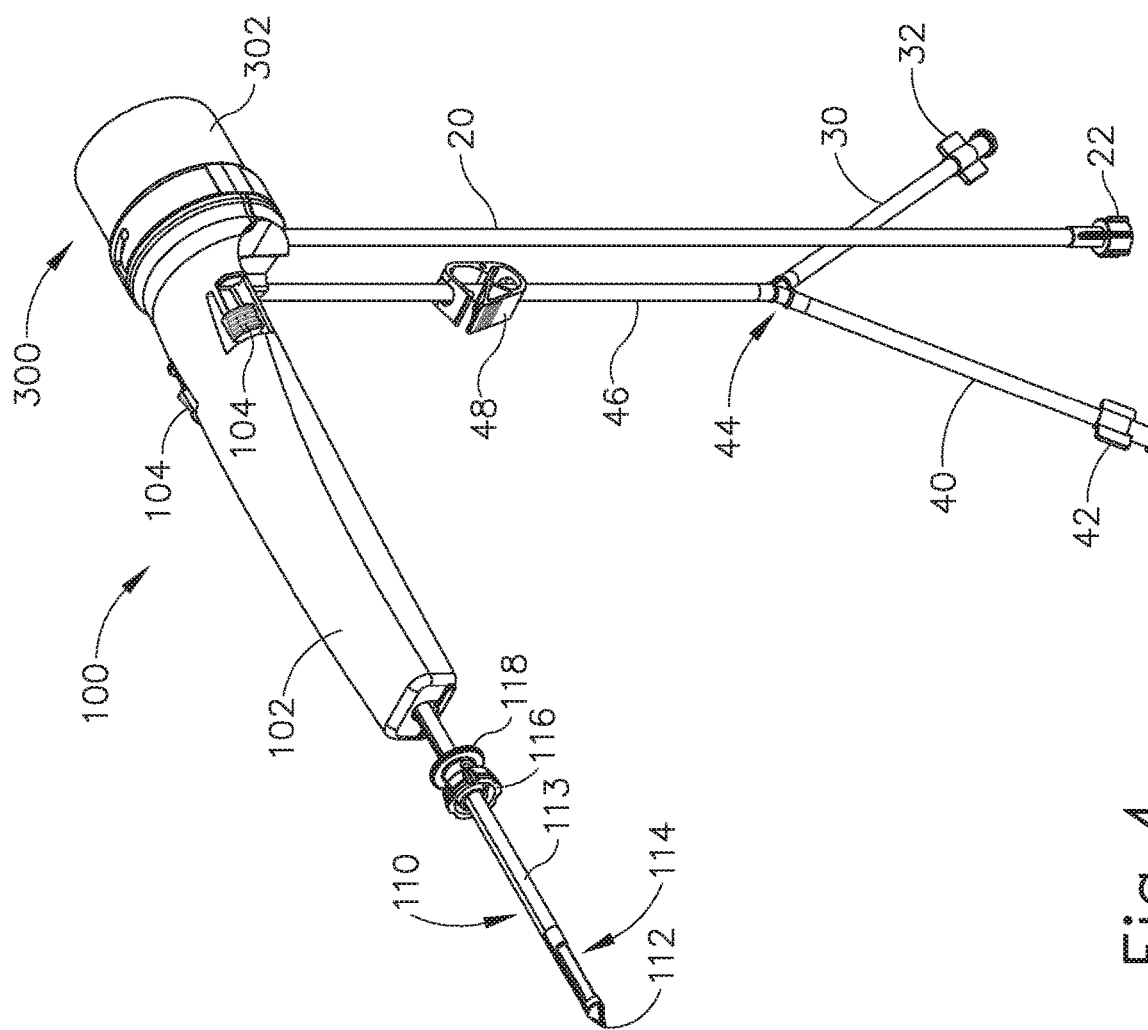
FIG. 4 depicts a perspective view of the probe of the biopsy device of FIG. 2.

A vacuum control module (250) is coupled with probe (100) via a valve assembly (90). In particular, vacuum control module (250) includes a tube set interface socket (252), which is configured to couple with valve assembly (90). Tube set interface socket (252) includes a pair of exposed spindles that are rotatably driven by motors (254, 256) to selectively actuate valve assembly (90). Valve assembly (90) is further coupled with a saline bag (80) via a tube (50); and with a vacuum canister (70) via a tube (60). Vacuum canister (70) is disposed in a vacuum canister receiving receptacle (258) of vacuum control module (250). Valve assembly (90) is coupled with probe (100) via a set of tubes (20, 30, 40). As shown in FIG. 4, each tube (20, 30, 40) includes a respective luer fitting (22, 32, 42) that is configured to provide a removable coupling with valve assembly (90). In the present example, vacuum control module (250) cooperates with valve assembly (90) to selectively provide vacuum, saline, atmospheric air, and fluid sealing to probe (100). By way of example only, such communication may be provided in accordance with at least some of the teachings of U.S. Pub. No. 2013/0218047, entitled "Biopsy Device Valve Assembly," published Aug. 22, 2013, the disclosure of which is incorporated by reference herein; and/or at least some of the teachings of U.S. Pub. No. 2014/0039343, entitled "Biopsy System," published Feb. 6, 2014, the disclosure of which is incorporated by reference herein.

Vacuum control module (250) is further coupled with holster (200) via a cable (210), which is operable to communicate electrical power to holster (200) and is further operable to communicate signals such as data and commands, etc., in a bi-directional fashion between holster (200) and vacuum control module (250). These components all cooperate to enable biopsy device (10) to acquire numerous tissue samples from a patient, such as from the patient's breast or other part of the patient's anatomy. By way of example only, such operability may be provided in accordance with at least some of the teachings of U.S. Pub. No. 2014/0039343, entitled "Biopsy System," published Feb. 6, 2014, the disclosure of which is incorporated by reference herein. In addition or in the alternative, such operability may be provided in accordance with any of the other references cited herein.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

II. Exemplary Probe

Figure 3:
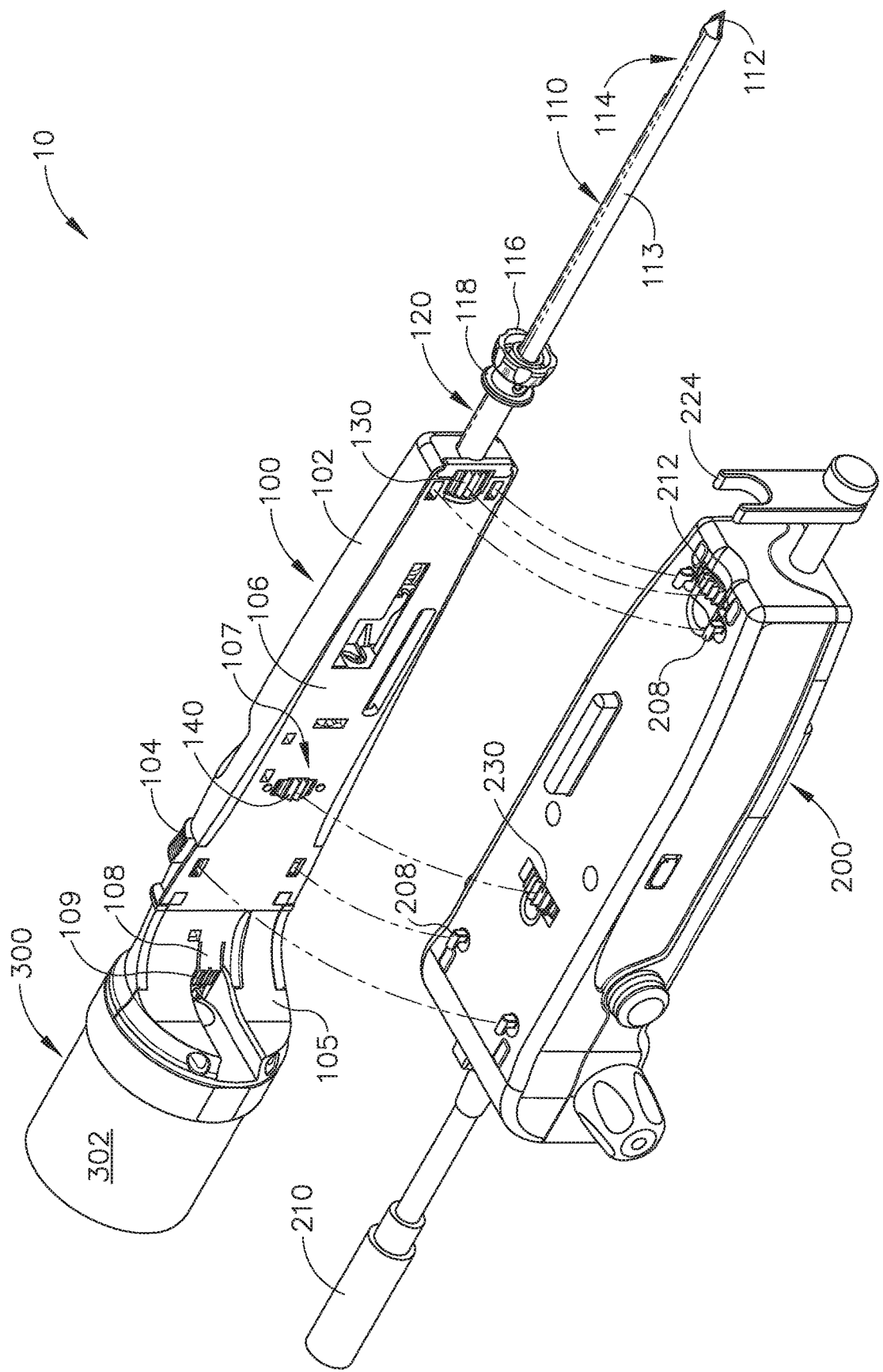
FIG. 3 depicts a perspective view of the biopsy device of FIG. 2, with the probe decoupled from the holster.

As shown in FIGS. 1-6, probe (100) of the present example includes a distally extending needle (110). Probe (100) also includes a chassis (106) and a top housing (102), which are fixedly secured together. As best seen in FIG. 3, a gear (140) is exposed through an opening (107) in chassis (106), and is operable to drive cutter actuation mechanism in probe (100). As also seen in FIG. 3, another gear (130) is exposed through chassis (106), and is operable to rotate needle (110) as will be described in greater detail below. Gear (140) of probe (100) meshes with exposed gear (230) of holster (200) when probe (100) and holster (200) are coupled together. Similarly, gear (130) of probe (100) meshes with exposed gear (212) of holster (200) when probe (100) and holster (200) are coupled together. It should be understood that holster (200) may be constructed and operable in accordance with at least some of the teachings of U.S. Pub. No. 2014/0039343, entitled "Biopsy System," published Feb. 6, 2014, the disclosure of which is incorporated by reference herein; and/or in accordance with at least some of the teachings of any other references cited herein.

A. Exemplary Needle Assembly

Needle (110) of the present example comprises a cannula (113) having a piercing tip (112), a lateral aperture (114) located proximal to tip (112), and a hub member (120). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pub. No. 2012/0310110, entitled "Needle Assembly and Blade Assembly for Biopsy Device," published Dec. 6, 2012, the disclosure of which is incorporated by reference herein. As another merely illustrative example, tip (112) may be configured in accordance with at least some of the teachings in U.S. Pub. No. 2013/0150751, entitled "Biopsy Device with Slide-In Probe," published Jun. 13, 2013, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (150) having a sharp distal edge (152) is located within needle (110). The interior of cutter (150) defines a lumen (151). Cutter (150) is operable to rotate and translate relative to needle (110) and past lateral aperture (114) to sever a tissue sample from tissue protruding through lateral aperture (114). For instance, cutter (150) may be moved from an extended position to a retracted position, thereby "opening"

lateral aperture (114) to allow tissue to protrude therethrough; then from the retracted position back to the extended position to sever the protruding tissue. As will be described in greater detail below, needle (110) may be rotated to orient lateral aperture (114) at any desired angular position about the longitudinal axis of needle (110). Such rotation of needle (110) is facilitated in the present example by hub member (120), which is described in greater detail below.

Figure 6:
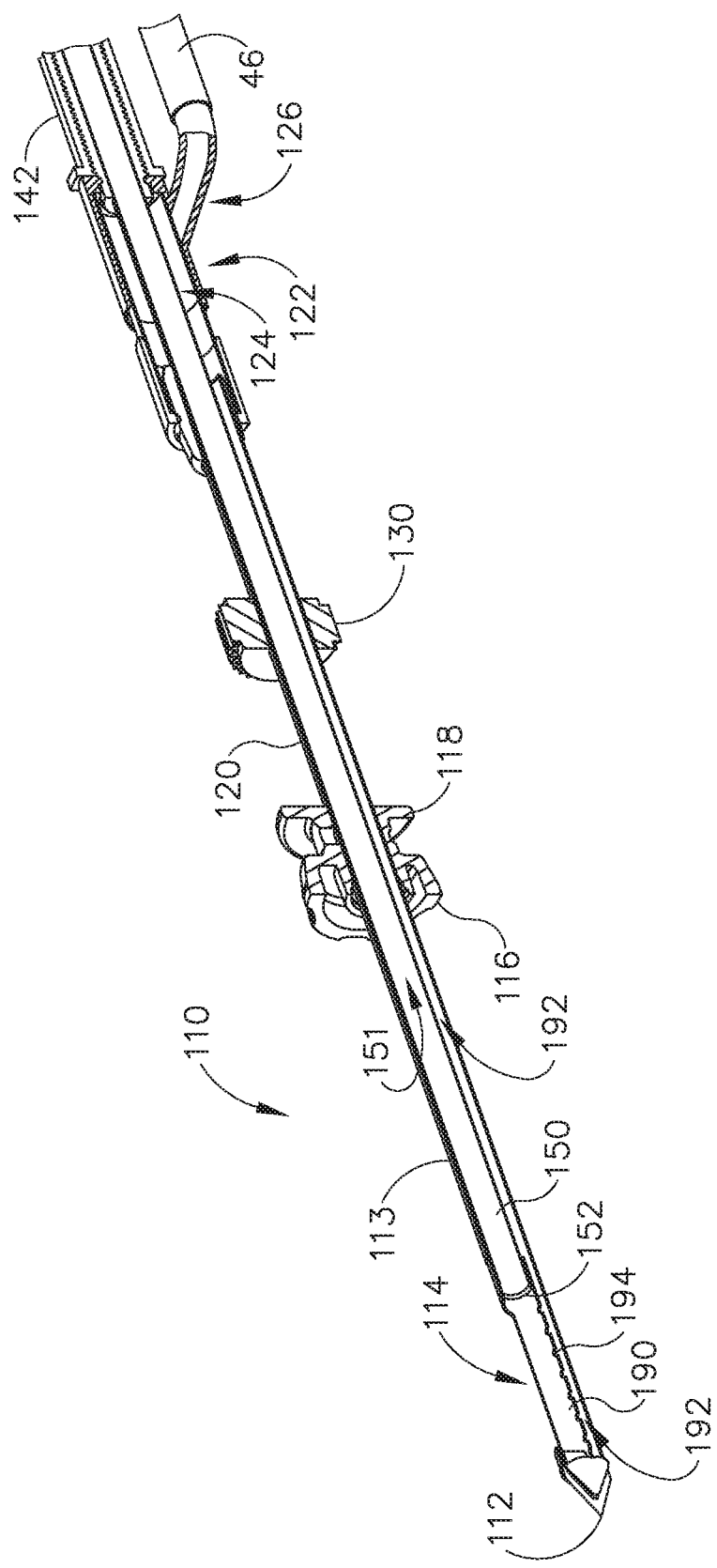
FIG. 6 depicts a cross-sectional view of a needle assembly of the probe of FIG. 4.

As best seen in FIG. 6, needle (110) also includes a sidewall (190) extending proximally from the proximal portion of tip (112). While wall (190) does not extend along the full length of cannula (113) in this example, it should be understood that wall (190) may extend the full length of cannula (113) if desired. Wall (190) defines a distal portion of a second lumen (192) that is lateral to and parallel to cutter (150). Wall (190) proximally terminates at a longitudinal position that is just proximal to the location of distal cutting edge (152) of cutter (150) when cutter (150) is in a proximal-most position as shown in FIG. 6. The exterior of cutter (150) and the interior of cannula (113) together define the proximal portion of second lumen (192) in the length of needle (110) that is proximal to the proximal end of wall (190).

Wall (190) includes a plurality of openings (194) that provide fluid communication between second lumen (192) and the region within cannula (113) that is above wall (190) and below lateral aperture (114). This further provides fluid communication between second lumen (192) and the lumen (151) defined by the interior of cutter (150), as will be described in greater detail below. Openings (194) are arranged such that at least one opening (194) is located at a longitudinal position that is distal to the distal edge of lateral aperture (114). Thus, the lumen (151) of cutter (150) and second lumen (192) may remain in fluid communication even when cutter (150) is advanced to a position where the distal cutting edge of cutter (150) is located at a longitudinal position that is distal to the longitudinal position of the distal edge of lateral aperture (114). An example of such a configuration is disclosed in U.S. Pat. No. 7,918,803, entitled "Methods and Devices for Automated Biopsy and Collection of Soft Tissue," issued Apr. 5, 2011, the disclosure of which is incorporated by reference herein. Of course, as with any other component described herein, any other suitable configurations may be used.

Hub member (120) of the present example is overmolded about needle (110), such that hub member (120) and needle (110) rotate and translate unitarily with each other. By way of example only, needle (110) may be formed of metal, and hub member (120) may be formed of a plastic material that is overmolded about needle (110) to unitarily secure and form hub member (120) to needle (110). Hub member (120) and needle (110) may alternatively be formed of any other suitable material(s), and may be secured together in any other suitable fashion. Hub member (120) includes an annular flange (118) and a thumbwheel (116). Gear (130) is slidably and coaxially disposed on a proximal portion of hub member (120) and is keyed to hub member (120), such that rotation of gear (130) will rotate hub member (120) and needle (110); yet hub member (120) and needle (110) may translate relative to gear (130). Gear (130) is rotatably driven by gear (212), as will be described in greater detail below. Alternatively, needle (110) may be rotated by rotating thumbwheel (116). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein. By way of example only, needle (110) may be translated longitudinally relative to chassis (106) and top housing (102), by a needle firing mechanism (224) in accordance with at least some of the teachings of U.S. Pub. No. 2012/0265095, entitled "Biopsy Device with Motorized Needle Firing, the disclosure of which is incorporated by reference herein.

As shown in FIGS. 4-7, a manifold (122) is provided at the proximal end of needle (110). Manifold (122) defines a hollow interior (124) and includes a port (126) in fluid communication with hollow interior (124). As best seen in FIG. 6, hollow interior (124) is also in fluid communication with second lumen (192) of needle (110). Port (126) is coupled with tube (46), such that manifold (122) provides fluid communication between second lumen (192) and tube (46). Manifold (122) also seals against the exterior of needle (110) such that manifold (122) provides a fluid tight coupling between second lumen (192) and tube (46) even if needle (110) is translated and/or rotated relative to manifold (122), such as during firing of needle (110) or re-orientation of needle (110), respectively. As shown in FIG. 4, tube (46) is coupled with tubes (30, 40) via a Y-fitting (44), such that tube (46) may receive vacuum, atmospheric air, saline, or medication from tubes (30, 40). In the present example, tube (40) is coupled with valve assembly (90) via luer fitting (42); while tube (30) is coupled with a source of medication (not show) via luer fitting (32). Thus, tube (46) and manifold (122) may provide vacuum, atmospheric air, or saline to second lumen (192) based on actuation of valve assembly (90); or medication to second lumen (192) based on actuation of a medication source. A clip (48) is operable to selectively close tube (46).

B. Exemplary Cutter Assembly

Figure 5:
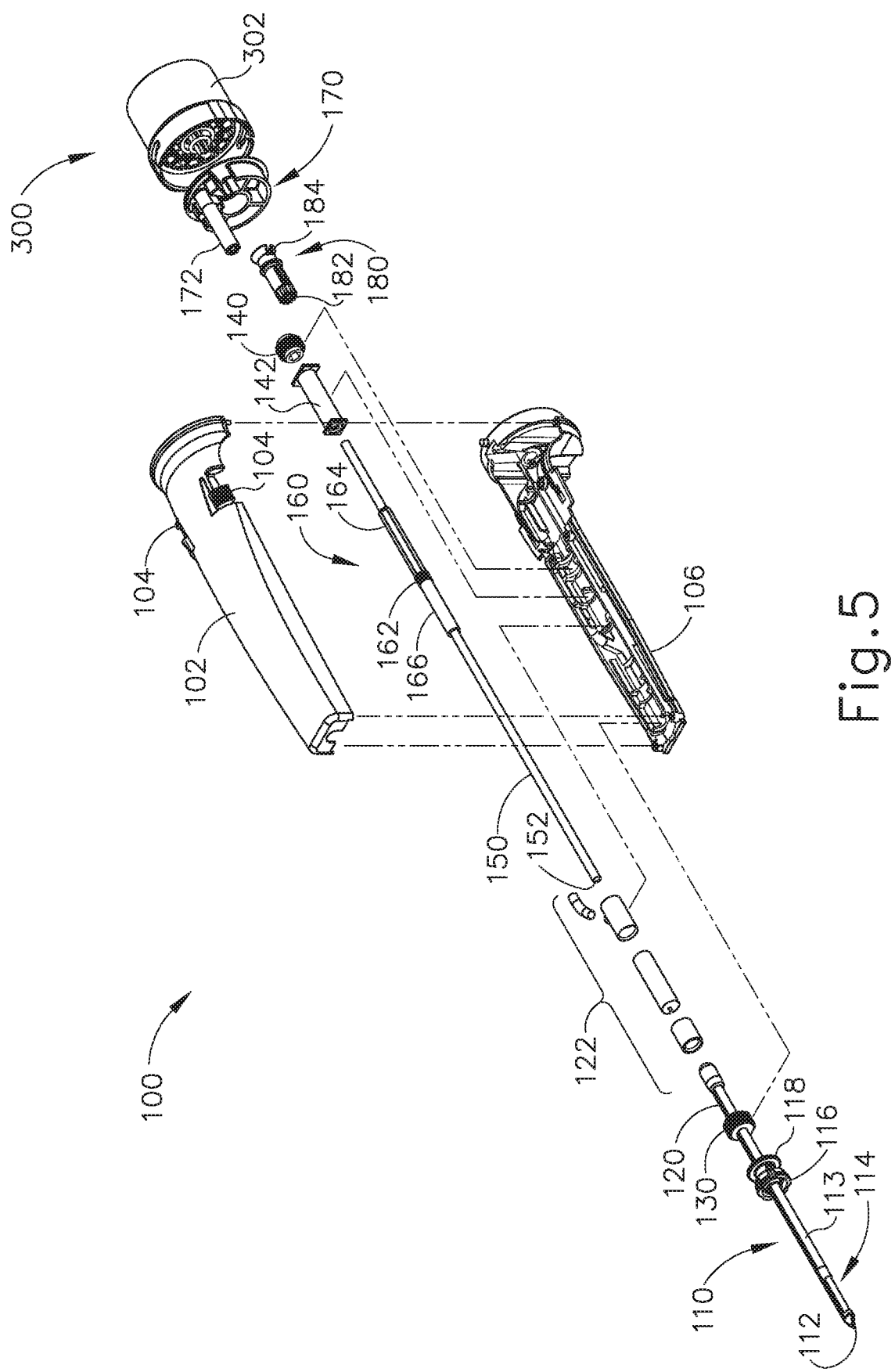
FIG. 5 depicts an exploded view of the probe of FIG. 4.
Figure 7:
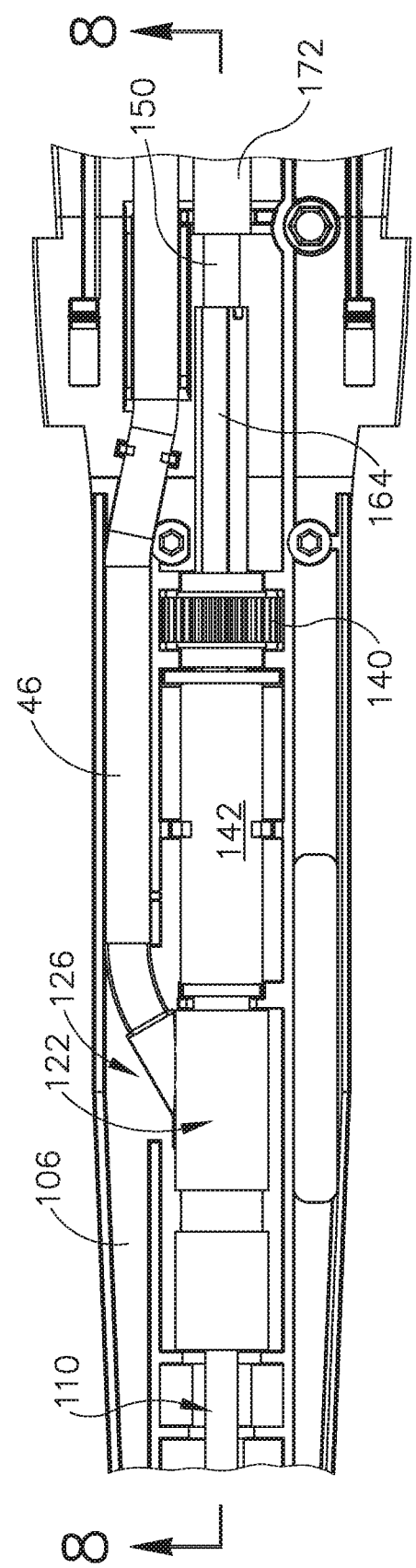
FIG. 7 depicts a partial top plan view of components of the probe of FIG. 4, with a top housing piece removed.
Figure 8:
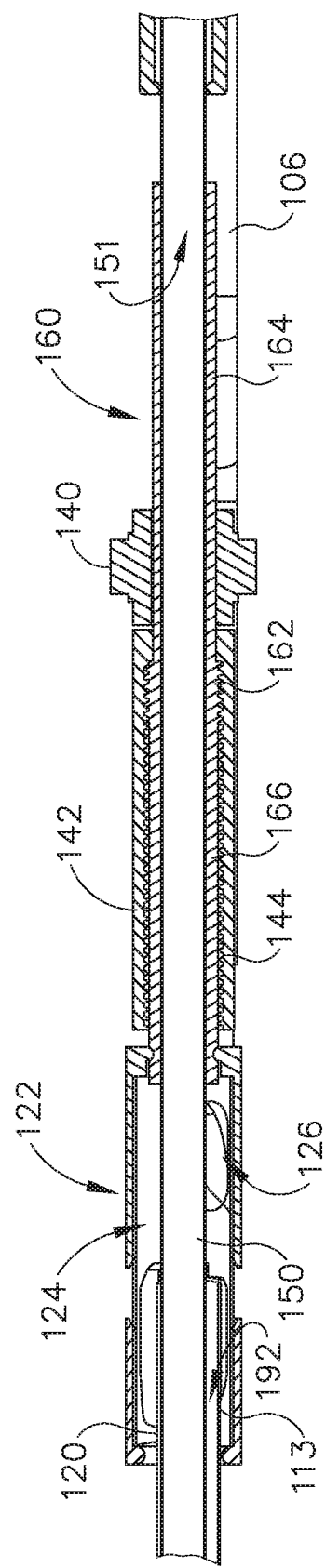
FIG. 8 depicts a cross-sectional view of the components of FIG. 7, taken along line 8-8 of FIG. 7.

As noted above, cutter (150) is operable to simultaneously translate and rotate relative to needle (110) to sever a tissue sample from tissue protruding through lateral aperture (114). As best seen in FIGS. 5 and 7-8 cutter (150) includes an overmold (160) that is unitarily secured to cutter (150). Overmold (160) includes a generally smooth and cylindraceous distal portion (166), threading (162) in a mid-region of overmold (160), and a set of hexagonal flats (164) extending along a proximal portion of overmold (160). Distal portion (166) extends into manifold (122). Manifold (122) seals against distal portion (166) such that manifold (122) such that manifold (122) maintains the fluid tight coupling between second lumen (192) and tube (46) even when cutter (150) is translated and rotated relative to manifold (122).

A gear (140) is positioned on flats (164) and includes a set of internal flats (not shown) that complement flats (164). Thus, gear (140) rotates overmold (160) and cutter (150) when gear (140) is rotated. However, overmold (160) is slidable relative to gear (140), such that cutter (150) may translate relative to chassis (160) despite gear (140) being longitudinally fixed relative to chassis (160). As noted above and as will be described in greater detail below, gear (140) is rotated by gear (230). As best seen in FIGS. 7-8, a nut (142) is associated with threading (162) of overmold (160). In particular, nut (142) includes internal threading (144) that meshes with threading (162) of overmold (160). Nut (142) is fixedly secured relative to chassis (160). Thus, when gear (140) rotates cutter (150) and overmold (160), cutter (150) will simultaneously translate due to the meshing of threading (144, 162). In some versions, the foregoing cutter actuation components are further configured in accordance with at least some of the teachings of U.S. Pat. Pub. No. 2008/0214955, the disclosure of which is incorporated by reference herein. As yet another merely illustrative example, cutter (150) may be rotated and/or translated using pneumatic motors, etc. Still other suitable ways in which cutter (150) may be actuated will be apparent to those of ordinary skill in the art in view of the teachings herein.

C. Exemplary Tissue Sample Holder Interface

Figure 10:
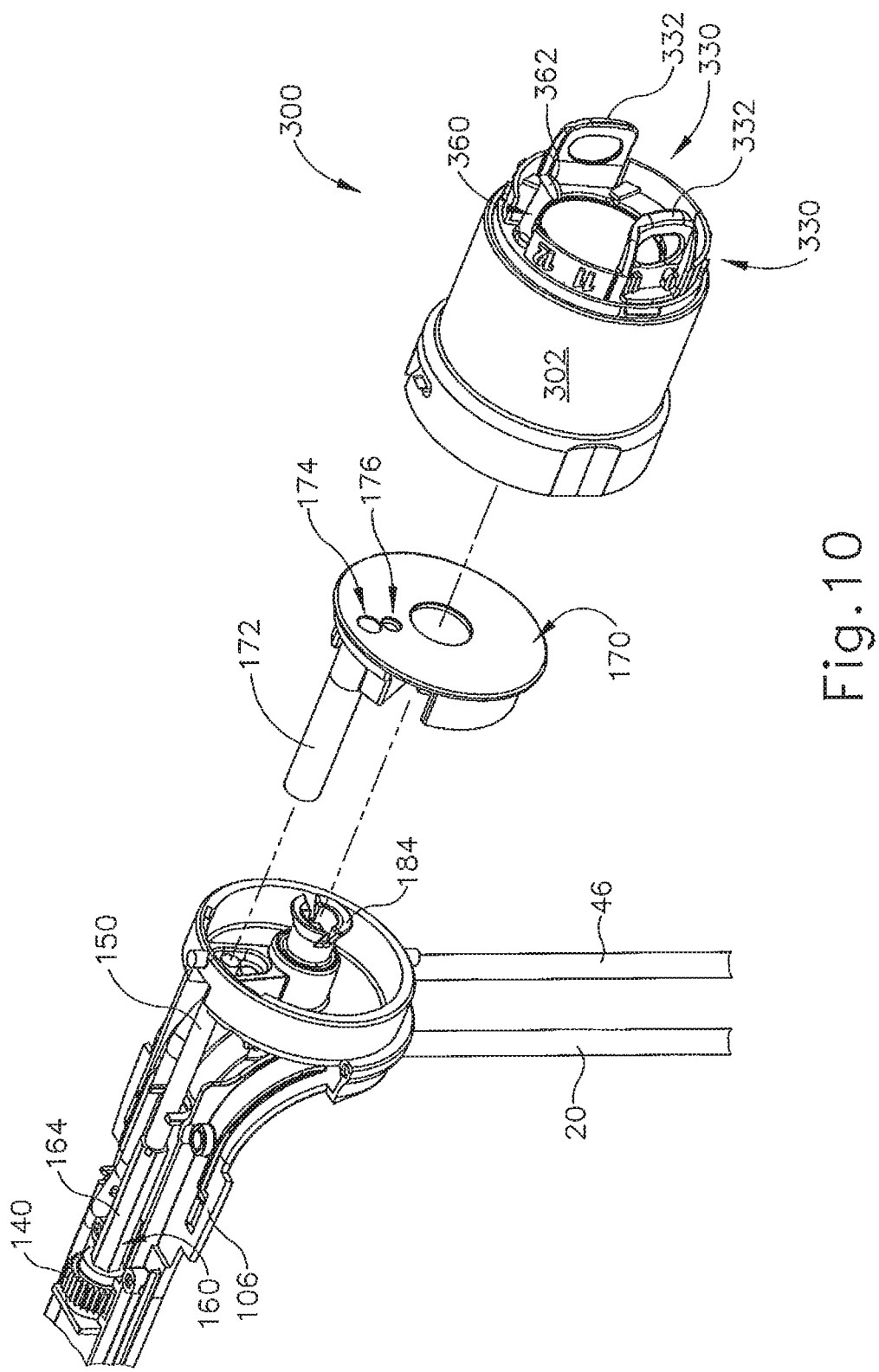
FIG. 10 depicts an exploded view of the tissue sample holder assembly of FIG. 9.
Figure 11:
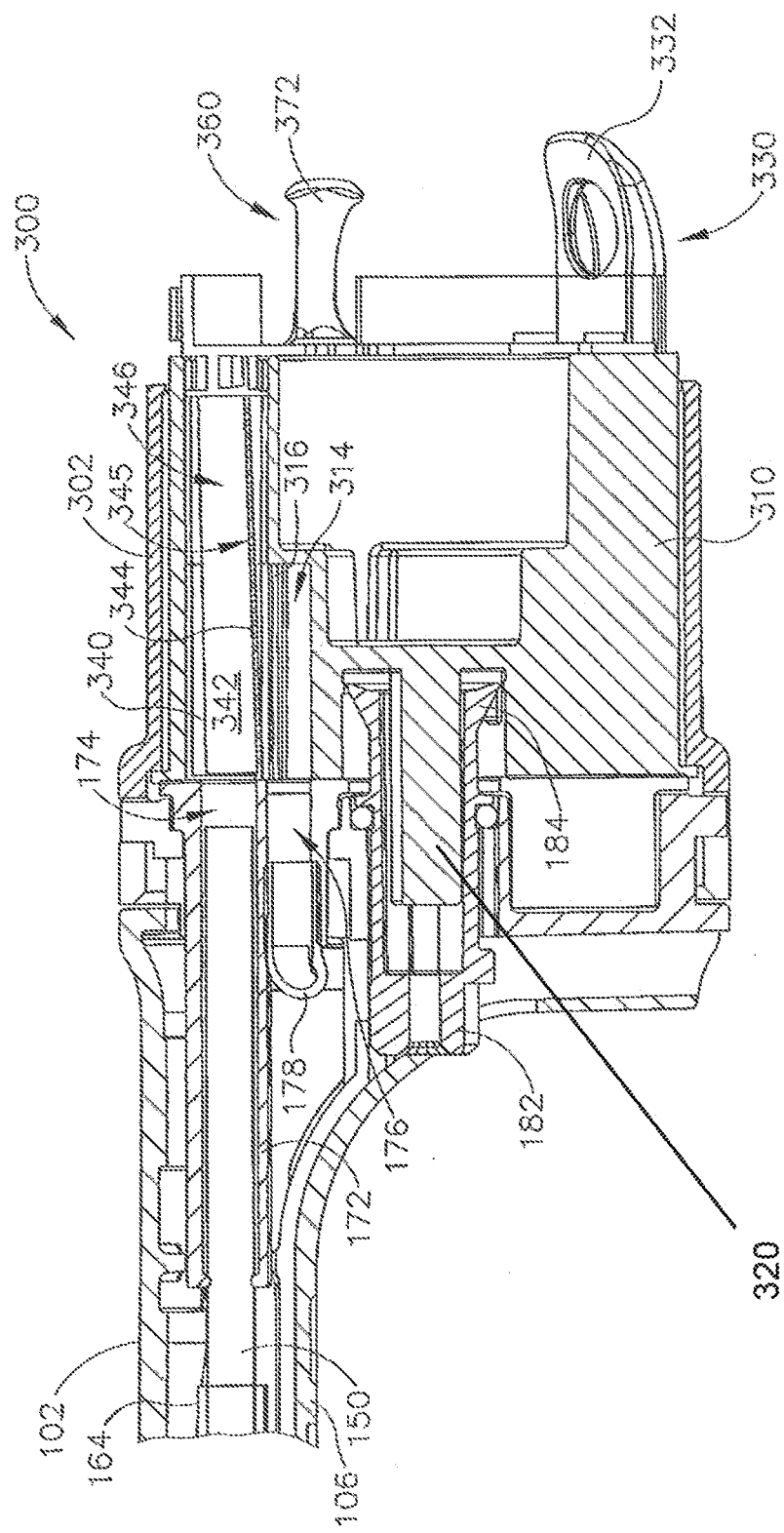
FIG. 11 depicts a cross-sectional side view of the tissue sample holder assembly of FIG. 9, with a tissue chamber aligned with the cutter.

As best seen in FIGS. 10-11, a sealing member (170) is provided at the proximal end of chassis (106) and interfaces with the distal face of a rotatable member (310) of tissue sample holder (300). In the present example, sealing member (170) comprises rubber, though it should be understood that any other suitable material(s) may be used. Sealing member (170) includes a longitudinally extending cutter seal (172), which receives cutter (150) and seals against the exterior of cutter (150). The proximal end of cutter (150) remains within cutter seal (172) throughout the full range of travel of cutter (150). Cutter seal (172) maintains a fluid tight seal against cutter (150) during this full range of motion, including during rotation and translation of cutter (150). An opening (174) is positioned at the proximal end of sealing member (170). It should be understood that opening (174) is in fluid communication with lumen (151) of cutter (150). It should also be understood that opening (174) is coaxially aligned with lumen (151) of cutter (150). Thus, severed tissue samples that are drawn proximally through lumen (151) of cutter (150) will ultimately exit proximally through opening (174) and into tissue sample holder (300) as will be described in greater detail below.

Figure 9:
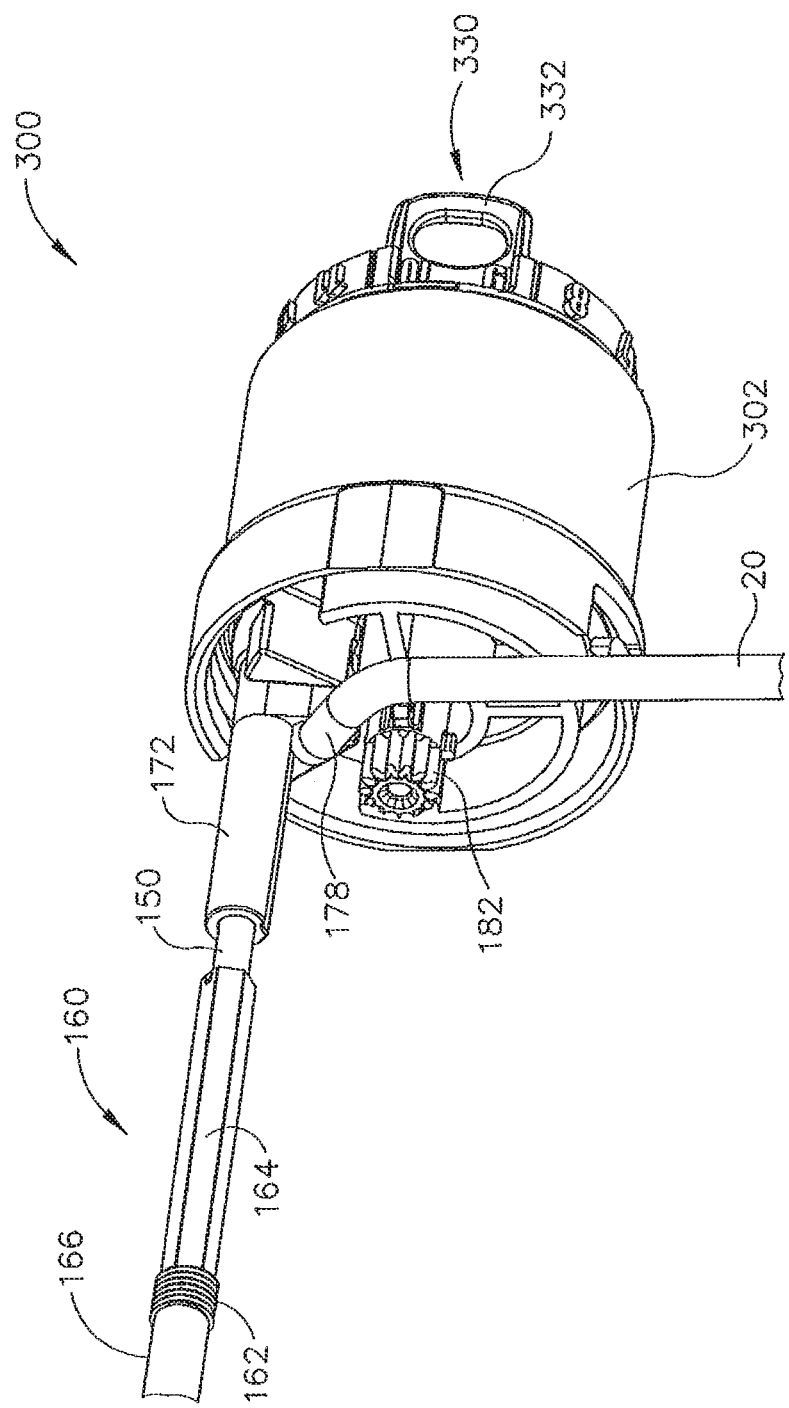
FIG. 9 depicts a perspective view of a tissue sample holder assembly of the probe of FIG. 4.

Sealing member (170) also includes another opening (176), which is positioned below opening (174). As best seen in FIGS. 9 and 11, opening (176) is in fluid communication with a port (178), which is coupled with tube (20). Thus, sealing member (170) provides fluid communication between tube (20) and opening (176) via port (178). Tube (20) is in fluid communication with a vacuum source at vacuum control module (250) as noted above, such that vacuum may be applied to opening (176). Such vacuum may further be communicated tao tissue sample holder (300), and ultimately to lumen (151) of cutter (150), as will be described in greater detail below.

As also seen in FIG. 10, chassis (106) includes a pair of outwardly extending bayonet pins (109), which are configured to secure tissue sample holder (300) to probe (100) as will be described in greater detail below.

III. Exemplary Tissue Sample Holder Assembly

Tissue sample holder (300) of the present example provides a plurality of discrete chambers that are configured to receive tissue samples that are severed by cutter (150) and communicated proximally through lumen (151) of cutter (150). In particular, tissue sample holder (300) includes tissue receiving trays (330) that are removably engaged with a rotatable member (310) or manifold. Rotatable member (310) is removably engaged with a grasping feature (184) of a rotation member (180). Rotation member (180) is longitudinally fixed relative to chassis (106) yet is rotatable relative to chassis (106). Rotation member (180) includes an integral gear (182), which meshes with gear (not shown) of holster (200) when probe (100) and holster (200) are coupled together. These gears (182) cooperate to rotate rotatable member (310) to index tissue chambers relative to lumen (151) of cutter (150) as will be described in greater detail below.

A transparent outer cup (302) or cover is positioned about rotatable member (310) and is removably secured to chassis (106). While bayonet features provide coupling between outer cup (302) and chassis (106), it should be understood that any suitable type of coupling may be used. Rotatable member (310) is freely rotatable within a chamber defined by outer cup (302). However, rotatable member (310) is engaged with outer cup (302) such that rotatable member (310) will decouple relative to chassis (106) when outer cup (302) is removed from chassis (106). In other words, rotatable member (310) may be selectively coupled with and removed relative to chassis (106) by coupling and removing outer cup (302) from chassis (106).

Rotatable member (310) of the present example generally comprises a rotatable body and defines a plurality of chambers in the form of passages that extend longitudinally through rotatable member (310) and that are angularly arrayed about the central axis of rotatable member (310). As shown in FIG. 11, a lateral recess (314) is associated with a distal portion of each passage (312). Shelves (316) demarcate boundaries between each passage (312) and the associate lateral recess (314). Passages (312) receive trays (330) while recesses (314) provide pneumatic passageways. An additional passage and a recess are associated with a plug (360). Rotatable member (310) also includes a central shaft (320), which is configured to removably engage grasping feature (184). Central shaft (320) couples with grasping feature (184) upon coupling of outer cup (302) with chassis (106), as described above. Engagement between central shaft (320) and grasping feature (184) provides rotation of rotatable member (310) upon rotation of gear (182).

As best seen in FIGS. 10-11, a sealing member (170) is provided at the proximal end of chassis (106) and interfaces with the distal face of rotatable member (310). In the present example, sealing member (170) comprises rubber, though it should be understood that any other suitable material(s) may be used. Sealing member (170) includes a longitudinally extending cutter seal (172), which receives cutter (150) and seals against the exterior of cutter (150). The proximal end of cutter (150) remains within cutter seal (172) throughout the full range of travel of cutter (150). Cutter seal (172) maintains a fluid tight seal against cutter (150) during this full range of motion, including during rotation and translation of cutter (150). An opening (174) is positioned at the proximal end of cutter seal (170). This opening (174) is configured to align with whichever passage (312, 313) is at the 12 o'clock position.

Another opening (176) is positioned below opening (174). Opening (176) is configured to align with whichever recess (314, 315) is at the 12 o'clock position. As best seen in FIGS. 9 and 11, opening (176) is in fluid communication with a port (178), which is coupled with tube (20). Thus, sealing member (170) provides fluid communication between tube (20) and whichever recess (314, 315) is at the 12 o'clock position. As will be described in greater detail below, rotatable member (310) further provides fluid communication between such recess (314, 315) and the associated passage (312, 313) at the 12 o'clock position; and thereby further to lumen (151) of cutter (150). In other words, sealing member (170) and rotatable member (310) cooperate to provide fluid communication between tube (20) and lumen (151) of cutter (150) via whichever passage (312, 313) and recess (314, 315) are at the 12 o'clock position. It should be understood that sealing member (170) of the present example maintains a fluid tight seal against the distal face of rotatable member (310), even as rotatable member (310) is rotated relative to sealing member (170).

As noted above, tissue sample holder trays (330) are configured to removably engage rotatable member (310). Each tissue sample holder tray (330) of the present example includes a grip (332), a proximal wall (334), and a plurality of strips (340) extending distally from proximal wall (334). Strips (340) are sized and configured for insertion into associated passages (312) of rotatable member (310). Each strip (340) includes a pair of sidewalls (344) and a floor (342). Each pair of sidewalls (344) and floor (342) together define a corresponding tissue sample chamber (346). An opening is provided at the distal end of each tissue sample chamber (346). Each opening of each tissue sample chamber (346) is sized and positioned to correspond with opening (174) of sealing member (170). Thus, the lumen (151) of cutter (150) is in fluid communication with the tissue sample chamber (346) of the strip (340) inserted in the passage (312) that is at the 12 o'clock position. As best seen in FIG. 11, strips (340) are configured such that the distal portion of each strip (340) receives support from a corresponding shelf (316) of rotatable member (310). Each floor (342) includes a plurality of openings (345) that provide fluid communication between tissue sample chamber (346) of strip (340) and lateral recess (314) of the passage (312) associated with strip (340). Thus, vacuum, atmospheric air, etc. that is communicated to opening (176) via tube (20) is further communicated to lumen (151) of cutter (150) via lateral recess (314), openings (345), and tissue sample chamber (346).

During operation of biopsy device (10), tissue samples severed by distal edge (152) of cutter (150) are communicated proximally through the lumen (151) of cutter (150) and are then deposited into the tissue sample chamber (346) that is aligned with lumen (151) of cutter (150). Rotatable member (310) is rotated to successively align tissue sample chambers (346) with lumen (151) of cutter (150), enabling several tissue samples to be separately deposited in different tissue sample chambers (346) during operation of biopsy device (10). Bodily fluids and saline, etc. that are pulled through lumen (151) will pass through tissue sample holder (300) and tube (20) and are eventually deposited in vacuum canister (70).

It should be understood that rotatable member (310) and/or trays (330) may be configured in numerous other ways. By way of example only, rotatable member (310) and/or trays (330) may be configured in accordance with at least some of the teachings of U.S. Pat. Pub. No. 2008/0214955, the disclosure of which is incorporated by reference herein. As another merely illustrative example, rotatable member (310) and/or trays (330) may be configured in accordance with at least some of the teachings of U.S. Pat. No. 8,702,623, the disclosure of which is incorporated by reference herein.

Tissue sample holder (300) of the present example includes a plug (360) that is received in a dedicated passage of rotatable member (310). Plug (360) includes a grip (362) and a longitudinally extending body. The body of plug (360) extends through part of the length of the corresponding dedicated passage of rotatable member (310). Plug (360) includes a pair of seals (not shown) that seal against the interior of the corresponding dedicated passage of rotatable member (310) when plug (360) is fully inserted in rotatable member (310). The corresponding dedicated passage of rotatable member (310) is configured to receive the shaft of a biopsy site marker applier. The corresponding dedicated passage of rotatable member (310) may also receive an instrument for delivering medicine, etc. to a biopsy site. By way of example only, the corresponding dedicated passage of rotatable member (310) may receive an adapter configured to provide an interface between the passage and a conventional medicine deliver device. In some other versions, plug (360) and/or the corresponding dedicated passage of rotatable member (310) are simply omitted.

FIGS. 12-18 show yet another exemplary tissue sample holder assembly (5900) that may be coupled with probe (100). Tissue sample holder assembly (5900) of this example comprises a cover (5910), a body (5920), a plurality of tissue sample trays (5940), and a plug (5980). Cover (5910) includes a pair of bayonet slots (5912) that are configured to receive bayonet pins (109), allowing tissue sample holder assembly (5900) to be removably coupled with probe (100). Cover (5910) also includes an open distal end (5914) and an open proximal end (5916). As will be described in greater detail below, cover (5910) is configured to contain body (5920) relative to probe (100), yet cover (5910) permits body (5920) to rotate within cover (5910).

Figure 12:
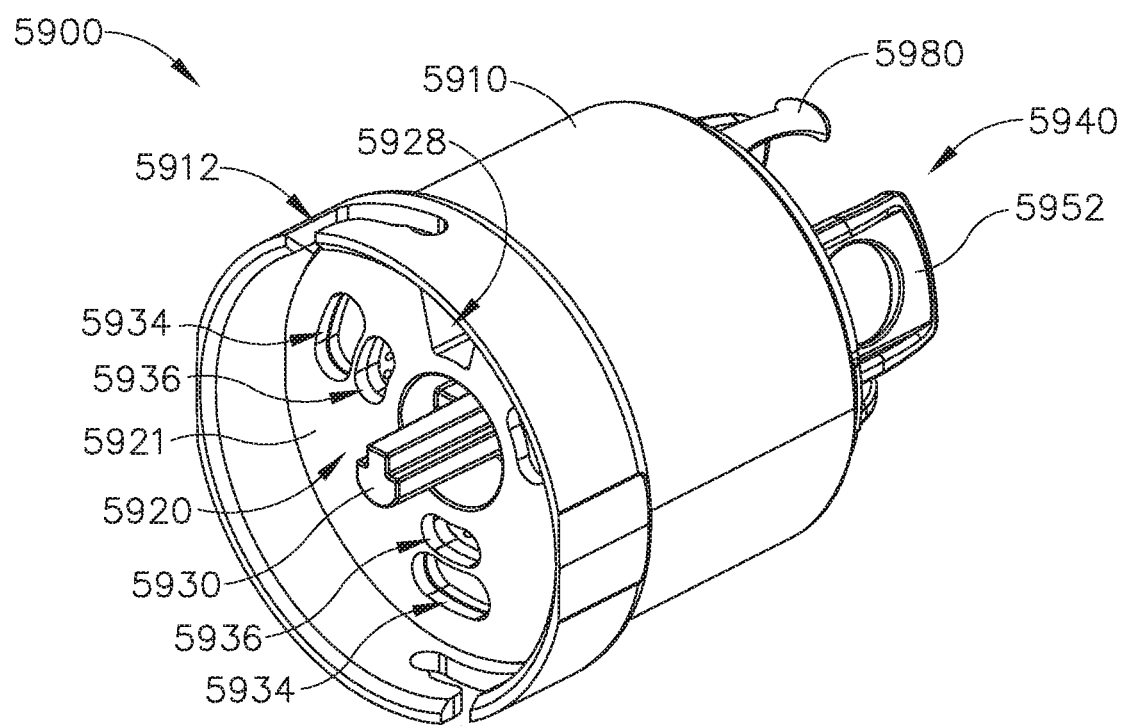
FIG. 12 depicts a perspective view of another exemplary alternative tissue sample holder assembly that may be incorporated into the probe of FIG. 4.
Figure 13:
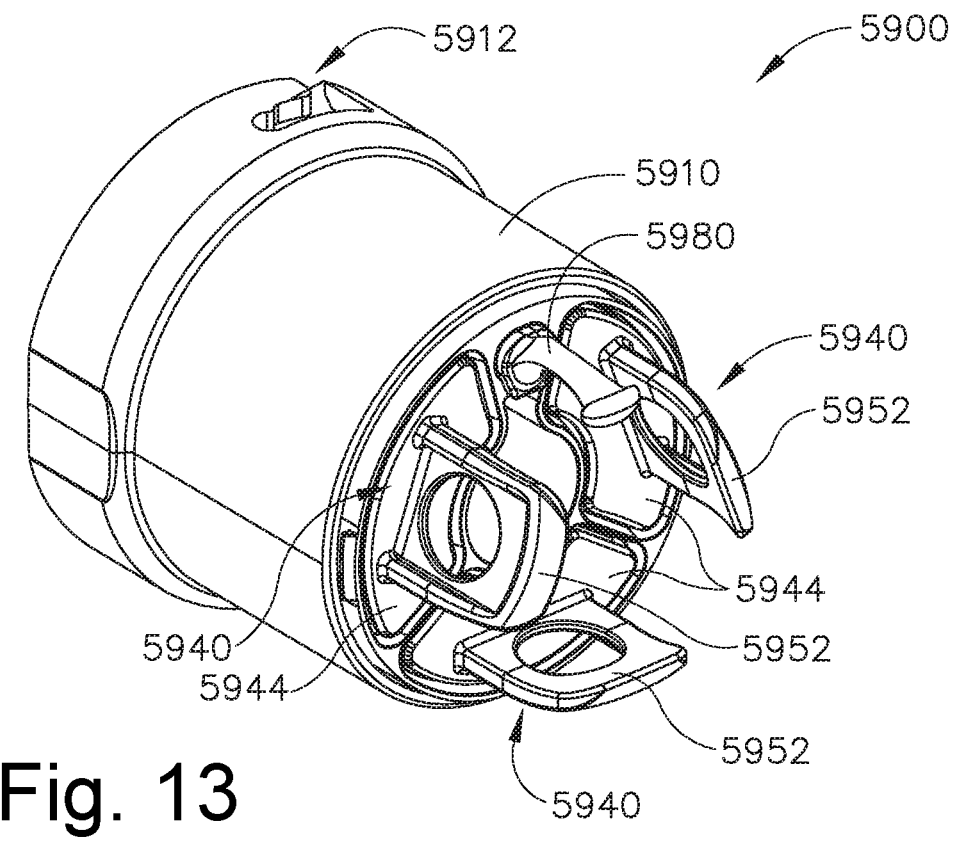
FIG. 13 depicts another perspective view of the tissue sample holder assembly of FIG. 12.
Figure 14:
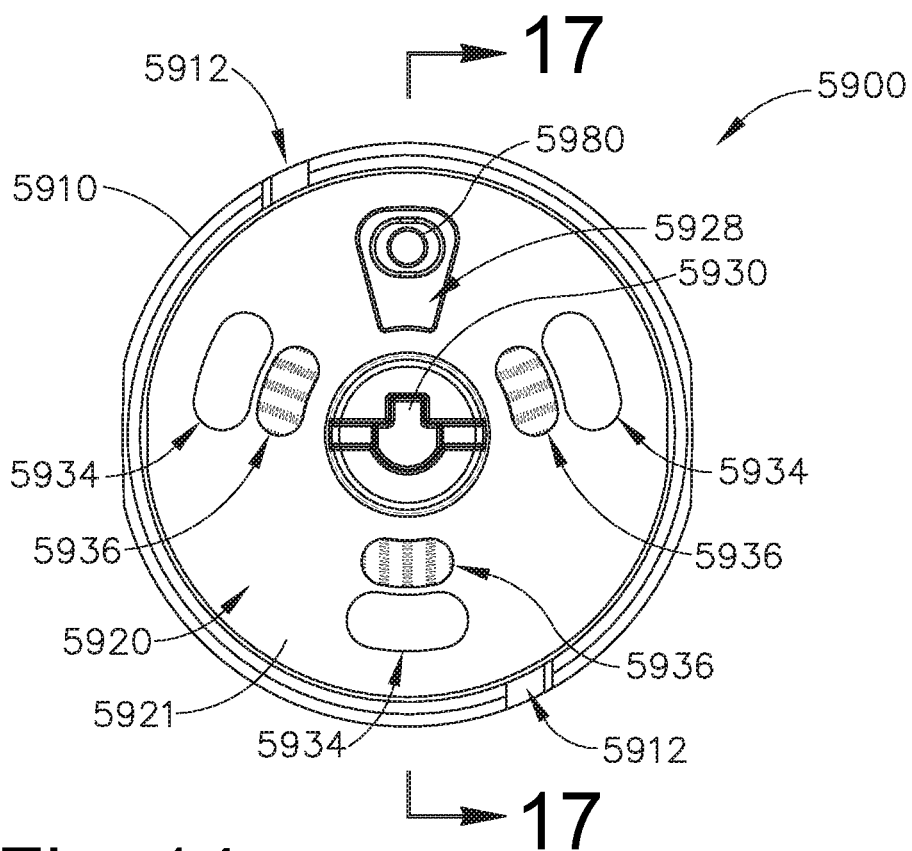
FIG. 14 depicts an end elevational view of the tissue sample holder assembly of FIG. 12.
Figure 15:
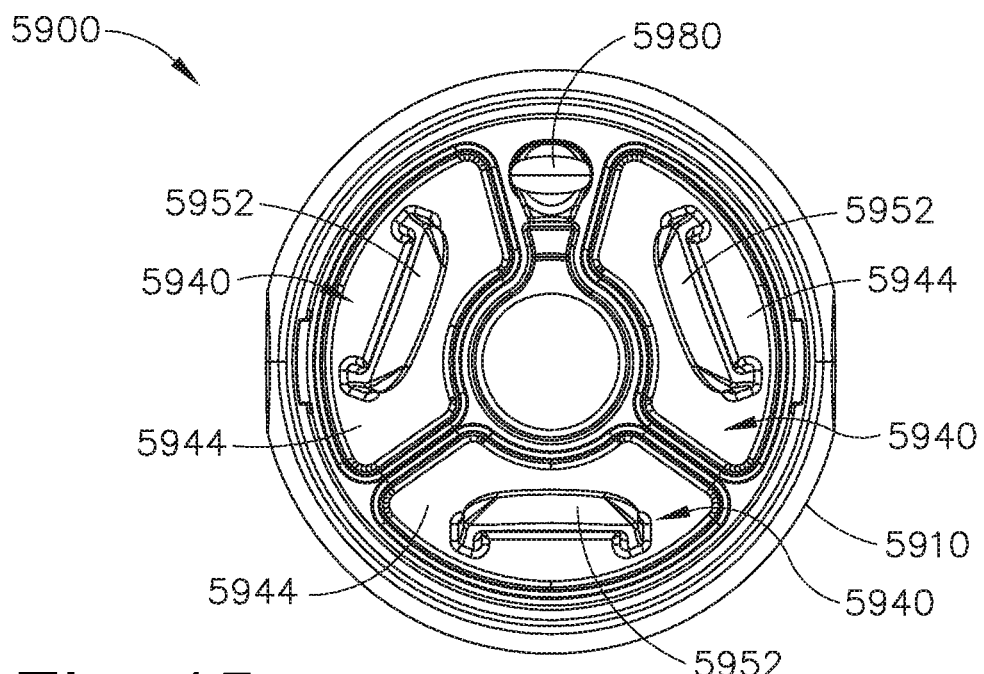
FIG. 15 depicts another end elevational view of the tissue sample holder assembly of FIG. 12.
Figure 16:
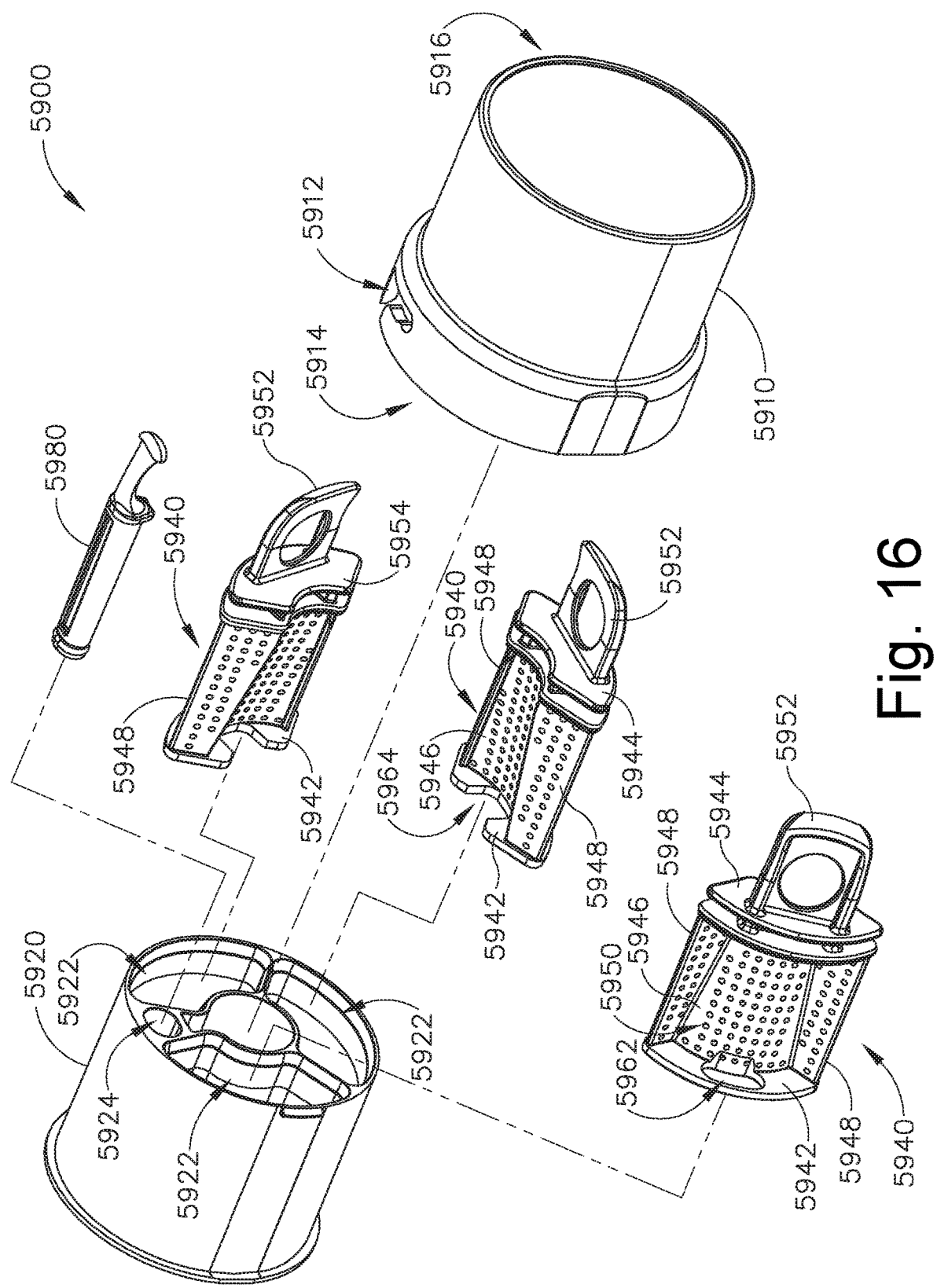
FIG. 16 depicts an exploded perspective view of the tissue sample holder assembly of FIG. 12.
Figure 17:
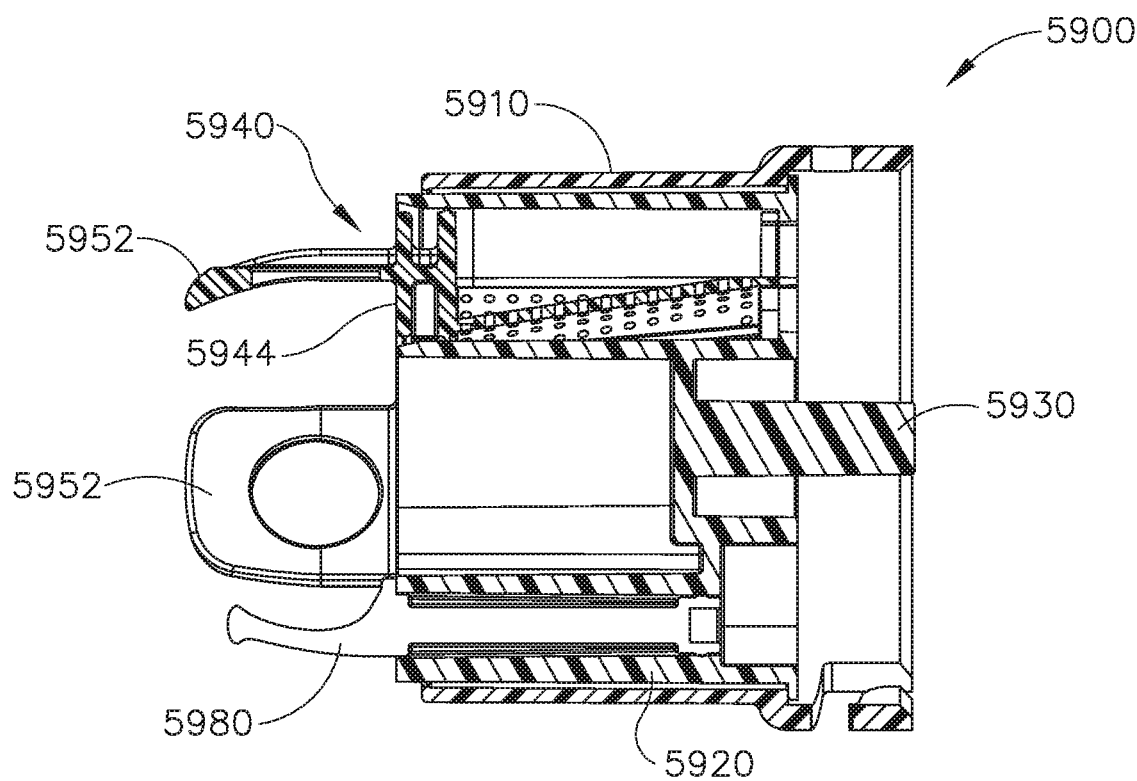
FIG. 17 depicts a cross-sectional side view of the tissue sample holder assembly of FIG. 12, taken along line 17-17 of FIG. 14.
Figure 18:
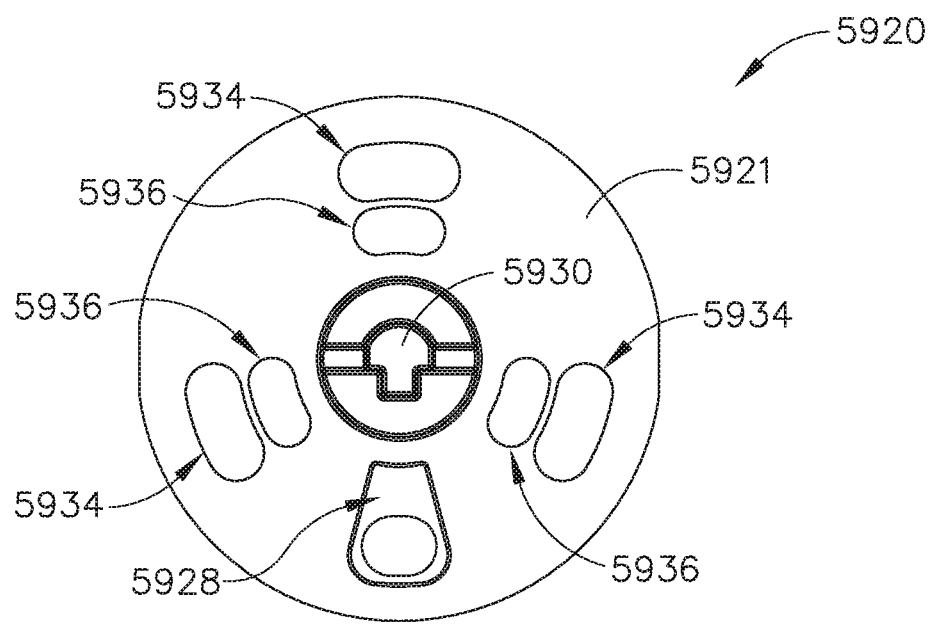
FIG. 18 depicts an end elevational view of a rotatable body of the tissue sample holder assembly of FIG. 12.
Figure 19:
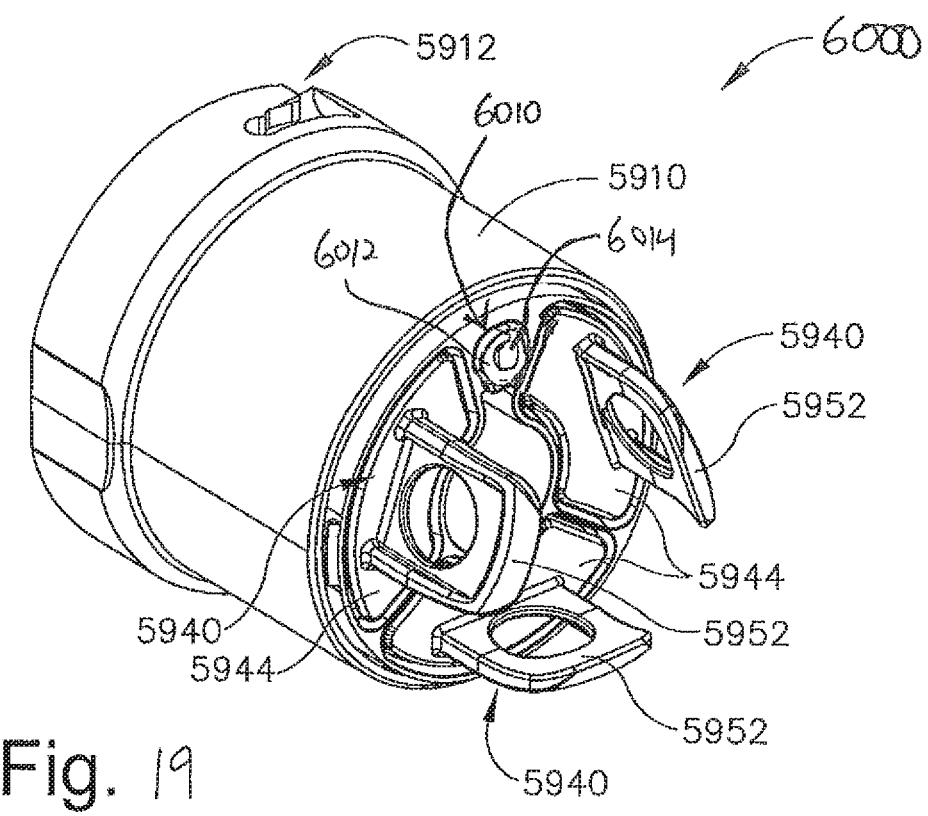
FIG. 19 depicts a perspective view of another exemplary alternative tissue sample holder assembly that may be incorporated into the probe of FIG. 4.
Figure 20:
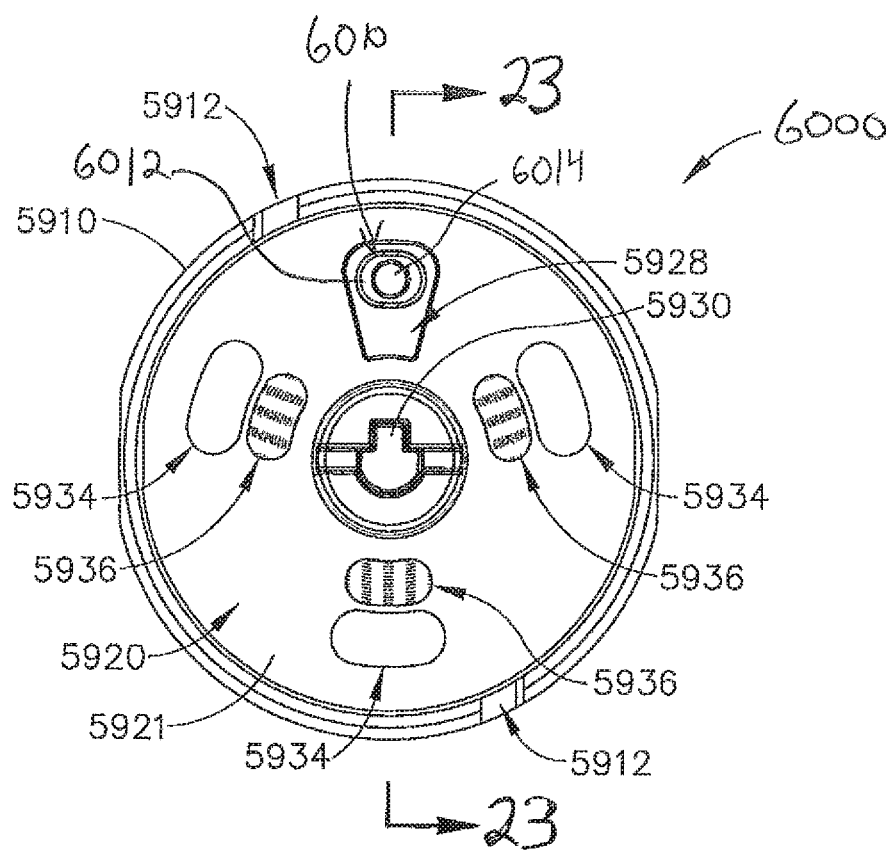
FIG. 20 depicts an end elevational view of the tissue sample holder assembly of FIG. 19.
Figure 21:
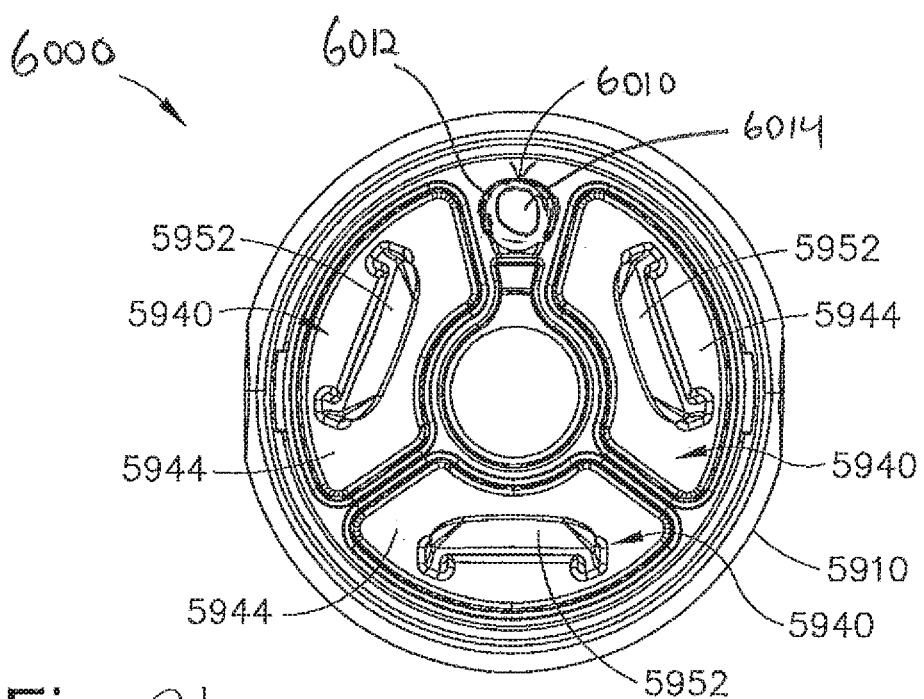
FIG. 21 depicts another end elevational view of the tissue sample holder assembly of FIG. 19.
Figure 22:
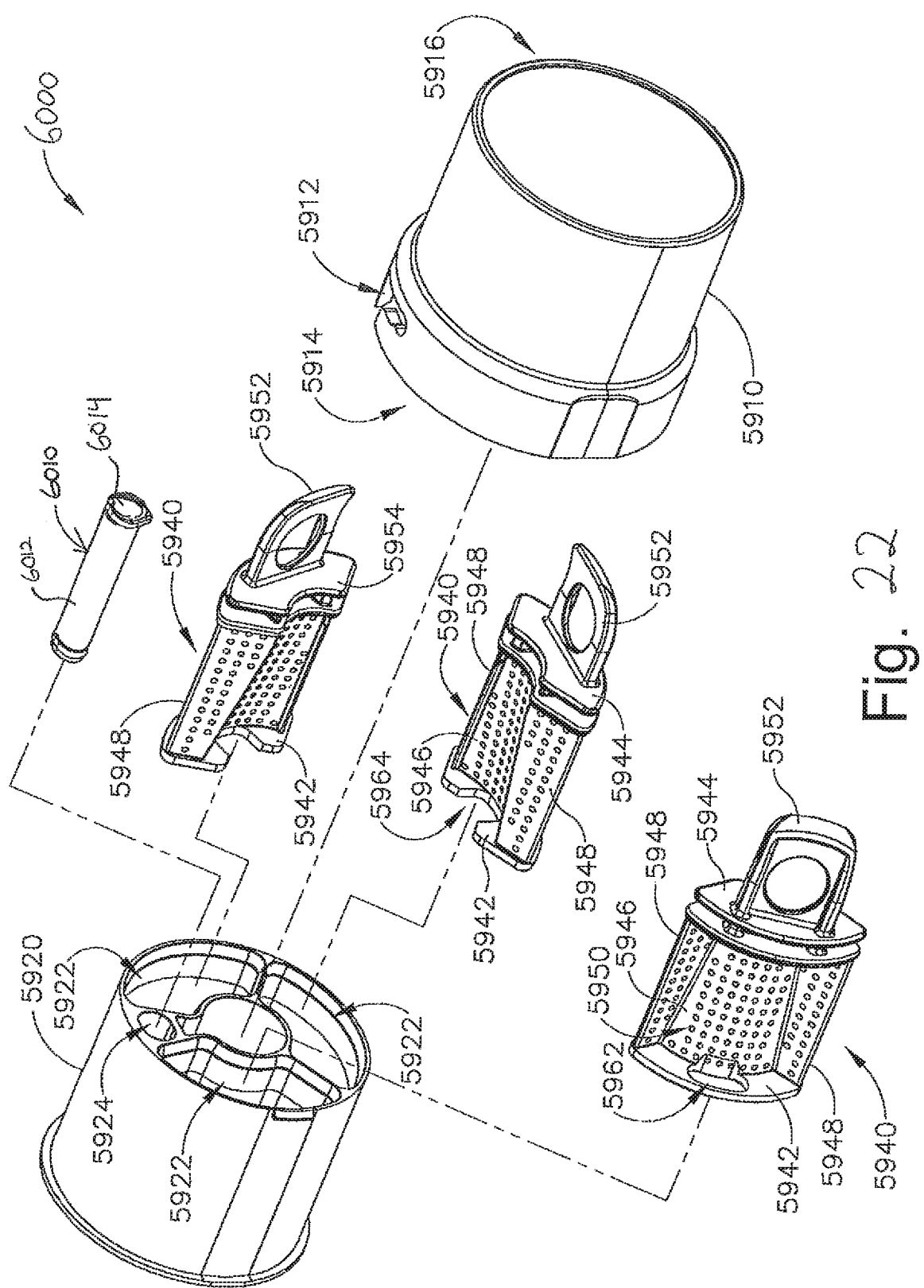
FIG. 22 depicts an exploded perspective view of the tissue sample holder assembly of FIG. 19.
Figure 23:
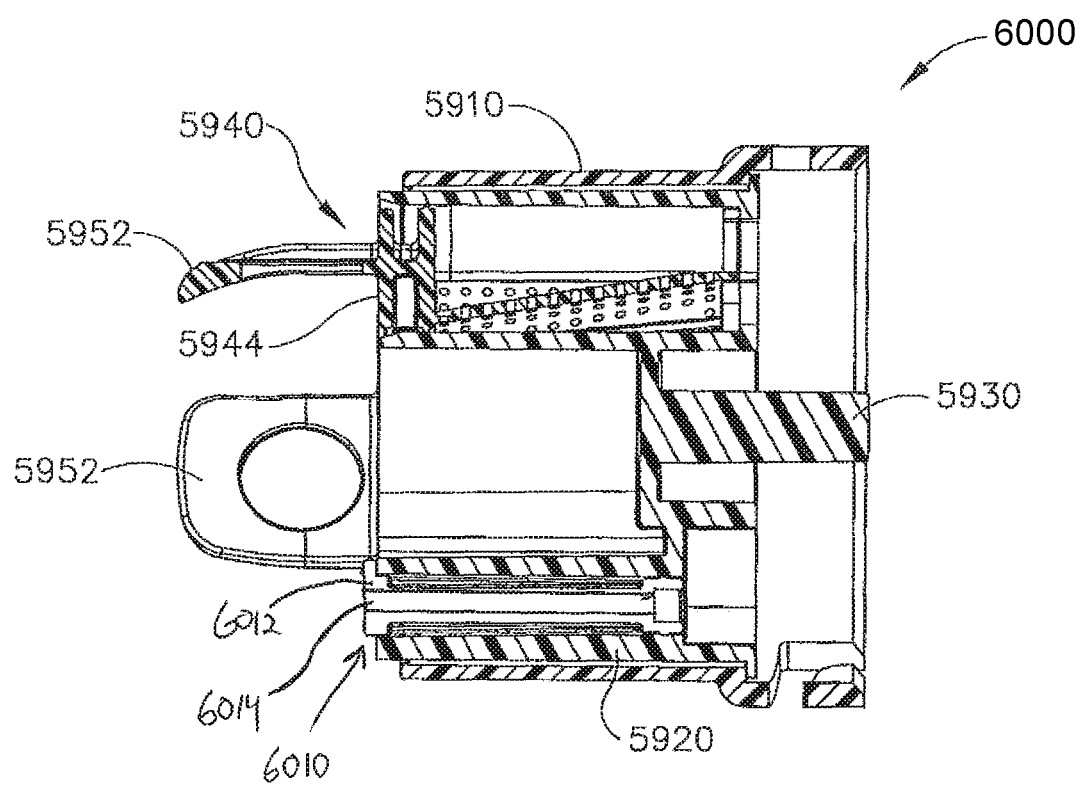
FIG. 23 depicts a cross-sectional side view of the tissue sample holder assembly of FIG. 19, taken along line 23-23 of FIG. 20.

As best seen in FIG. 16, body (5920) includes a plurality of tray receiving passageways (5922) and a plug receiving passageway (5924), each passageway (5922, 5924) extending proximally from the distal end (5921) of body (5920). Passageways (5922) are configured to receive tissue sample trays (5940); while passageway (5924) is configured to receive removable plug (5980). As described above with respect to plug (360), plug (5980) of the present example stops short of the full length of passageway (5924) when plug (5980) is fully inserted in passageway (5924), such that a recess (5928) remains in the distal end of passageway (5924) when plug (5980) is fully inserted in passageway (5924). As shown in FIGS. 12, 14, and 17, the distal wall (5932) of body (5920) includes a set of upper openings (5934) and a set of lower openings (5936) for each respective passageway (5922). When tissue sample holder (5900) is coupled with probe (100) and body (5920) is indexed to one of three tissue sample receiving angular positions relative to probe (100), a corresponding upper opening (5934) aligns with opening (174) of sealing member (170); while a corresponding lower opening (5936) aligns with opening (176) of sealing member (170). Thus, a given upper opening (5934) is in fluid communication with lumen (151) of cutter (150) when body (5920) is indexed to a given tissue sample receiving angular position relative to probe (100); and a given lower opening (5936) is in fluid communication with tube (20) when body (5920) is indexed to a given tissue sample receiving angular position relative to probe (100).

As best seen in FIGS. 12, 14 and 17, body (5920) also includes a distally projecting stud (5930). Stud (5930) is configured to couple with grasping feature (184) of rotation member (180). Stud (5930) is a unitary feature of body (5920), such that rotation of stud (5930) will rotate body (5920) about the longitudinal axis of stud (5930). As noted above, rotation member (180) includes an integral gear (182), which meshes with gear (240) of holster (200) when probe (100) and holster (200) are coupled together. Gear (240) is driven by a motor in holster (200) to rotate rotation member (180) in predetermined angular increments each time cutter (150) is actuated to sever a tissue sample. By way of example only, gear (240) may be driven in accordance with at least some of the teachings of U.S. Pub. No. 2014/0039343, entitled "Biopsy System," published Feb. 6, 2014, the disclosure of which is incorporated by reference herein; and/or in accordance with at least some of the teachings of any other references cited herein.

As best seen in FIGS. 16 and 17 each tissue sample tray (5940) comprises a distal wall (5942), a proximal wall (5944), a floor (5946), and a pair of sidewalls (5948) extending between walls (5942, 5944). Walls (5942, 5944, 5948), and floor (5946) cooperate to define a tissue receiving compartment (5950). In particular, floor (5946) slopes downwardly as floor (5946) extends proximally from distal wall (5942). Correspondingly, side walls (5948) expand as side walls (5948) extend proximally from distal wall (5942) to accommodate the downwardly sloping floor (5946). A handle (5952) extends proximally from proximal wall (5944), facilitating proximal withdrawal of tissue sample tray (5940) from passageway (5922). Distal wall (5942) defines an upper opening (5962) and a lower recess (5964). Opening (5962) and recess (5964) are configured to align with corresponding openings (5934, 5936) of body (5920) and openings (174, 176) of sealing member (170) when tissue sample holder (5900) is coupled with probe (100). Thus, a given upper opening (5962) is in fluid communication with lumen (151) of cutter (150) when body (5920) is indexed to a given tissue sample receiving angular position relative to probe (100); and a given lower recess (5964) is in fluid communication with tube (20) when body (5920) is indexed to a given tissue sample receiving angular position relative to probe (100).

Upper opening (5962) is in direct fluid communication with tissue receiving compartment (5950). Lower recess (5964) is in fluid communication with a gap or space below floor (5946). In the present example, a plurality of drainage apertures (5970, 5972) are formed through walls (5948) and floor (5946), respectively. Drainage apertures (5970, 5972) are configured and operable substantially identically to the various drainage apertures described above. It should be understood that, when vacuum from tube (20) is applied through openings (176, 5936) and recess (5964), such vacuum will be communicated to the gap or space defined between the outer surface of floor (5946) and the inner surface of passageway (5922); and to the gap or space defined between the outer surfaces of sidewalls (5948) and the inner surface of passageway (5922). It should further be understood that fluid drained from tissue receiving compartment (5950) may be drawn out via openings (5968), recess (5964), and opening (176).

It should be understood from the foregoing that, when tissue sample holder (5900) is coupled with probe (100), with body (5920) indexed to a given tissue sample receiving angular position relative to probe (100), upper openings (5934, 5962) align with opening (174) of sealing member (170); while a given lower opening (5936) and recess (5964) align with opening (176) of sealing member (170). Thus, when vacuum is applied via tube (20) and opening (176), this vacuum is communicated through lower opening (5936), and recess (5964) to a gap defined between floor (5946) and the inner surface of passageway (5922). This vacuum is further communicated through drainage openings (5970, 5972) to tissue receiving compartment (5950); and further to openings (5962, 5934, 174) to reach lumen (151) of cutter (150). It should therefore be understood that vacuum from tube (20) may draw severed tissue samples proximally through lumen (151) to reach tissue receiving compartment (5950). It should also be understood that fluids drawn proximally through lumen (151) may be further drawn into tube (20) via openings (174, 5934, 5962), tissue receiving compartment (5950), drainage openings (5970, 5972), recess (5964) and openings (5936, 176). Thus, when tissue sample holder (5900) is coupled with probe (100), with body (5920) indexed to a given tissue sample receiving angular position relative to probe (100), biopsy device (10) may be operated to capture tissue samples in tissue receiving compartment (5950) and drain fluids.

In some instances, the operator may wish to administer one or more fluids (e.g., medication(s) and/or other kinds of fluids) to the biopsy site. In such instances, the motor that drives rotation member (180) may be activated to rotate body (5920) to align passageway (5924) with openings (174, 176). At this stage, plug (5980) may be inserted in passageway (5924) such that openings (174, 176) are presented with sealed recess (5928). As in other examples described herein, recess (5928) provides a short circuit coupling openings (174, 176) together, bypassing tissue sample trays (5940).

In addition or in the alternative, the operator may wish to deploy a biopsy site marker to the biopsy site via needle (110). In such instances, body (5920) may be rotated to align passageway (5924) with openings (174, 176). At this stage, plug (5980) may be removed from passageway (5924), providing an open path to lumen (151) of cutter (150) via passageway (5924) and opening (174). Cutter (150) may be in a proximally retracted position at this stage, effectively opening lateral aperture (114). The shaft of a marker applier instrument may then be inserted through passageway (5924), opening (174), and lumen (151) of cutter (150) until the working end of the marker applier instrument reaches the open lateral aperture (114). The marker applier instrument may then be actuated to deploy the biopsy site marker at the biopsy site via the open lateral aperture (114). An exemplary marker applier instrument is disclosed in U.S. Pub. No. 2014/0039343, entitled "Biopsy System," published Feb. 6, 2014, the disclosure of which is incorporated by reference herein. Alternatively, any other suitable marker applier instrument may be used. Once the biopsy site has been suitably marked, the operator may replace plug (5980) in passageway (5924). Of course, some variations may lack plug (5980) and plug receiving passageway (5924) altogether. Plug (5980) and plug receiving passageway (5924) are merely optional.

IV. Exemplary Tissue Sample Holder Assembly with Filter Feature

As noted above, it may be desirable to provide medication to a biopsy site while needle (110) is disposed in the tissue. In particular, the operator may actuate biopsy device (10) to obtain at least one tissue sample while needle (110) is disposed in the tissue; then deliver one or more medications to the biopsy site via needle (110) while needle (110) remains disposed at the biopsy site. As also noted above, tube (30) may be coupled with a source of medication via luer fitting (32). FIGS. 19-25 show an exemplary alternative tissue sample holder (6000), representing a variation of tissue sample holder (5900) described above, that may be used with biopsy device (10) to facilitate delivery of medication to a biopsy site. Tissue sample holder (6000) of the present example is substantially similar to tissue sample holder (5900) described above, such that like numerals will indicate like components without further discussion of these components. Unlike tissue sample holder (5900), tissue sample holder (6000) of the present example includes a filter assembly (6010) instead of a plug (5980).

Filter assembly (6010) of the present example comprises a body (6012) and a filter medium (6014). Body (6012) is configured to fit in passageway (5924) of body (5920) of tissue sample holder assembly (5900) and thereby secure filter assembly (6010) in body (5920). Filter medium (6014) comprises a material that is hydrophobic yet allows air to pass through. By way of example only, filter medium (6014) may comprise a 5-micron copolymer acrylic membrane. Other suitable materials that may be used to form filter medium (6014) will be apparent to those of ordinary skill in the art in view of the teachings herein.

While filter medium (6014) is shown as being disposed in an elongate body (6010) in passageway (5924), filter medium (6014) may instead be integrated into tissue sample holder assembly (5900) in numerous other ways. By way of example only, some variations of body (5920) may lack passageway (5924); and filter medium (6010) may be integrated into an opening associated with one of passageways (5922), with the modified passageway (5922) being rendered incapable of receiving tissue samples. Other ways in which filter medium (6010) may be integrated into tissue sample holder assembly (5900) (and variations of tissue sample holder assembly (5900)) will be apparent to those of ordinary skill in the art in view of the teachings herein.

During a biopsy procedure, after the operator has obtained a desired number of biopsy samples from the patient's tissue, the operator may cause body (5920) to rotate such that filter assembly (6010) is aligned with openings (174, 176) of sealing member (170). In some versions, this may be accomplished by the operator manually rotating body (5920). In some other versions, this may be accomplished by a motor rotating body (5920). For instance, the operator may provide an input at a user interface provided through vacuum control module (250), indicating that the operator wishes to administer medication at the biopsy site. In response, vacuum control module (250) may command a motor in holster (200) to rotate gear (182) to thereby rotate body (5920) until filter assembly (6010) is aligned with openings (174, 176) of sealing member (170). The operator may then administer medication to the biopsy site via needle (110), as described below.

Figure 24:
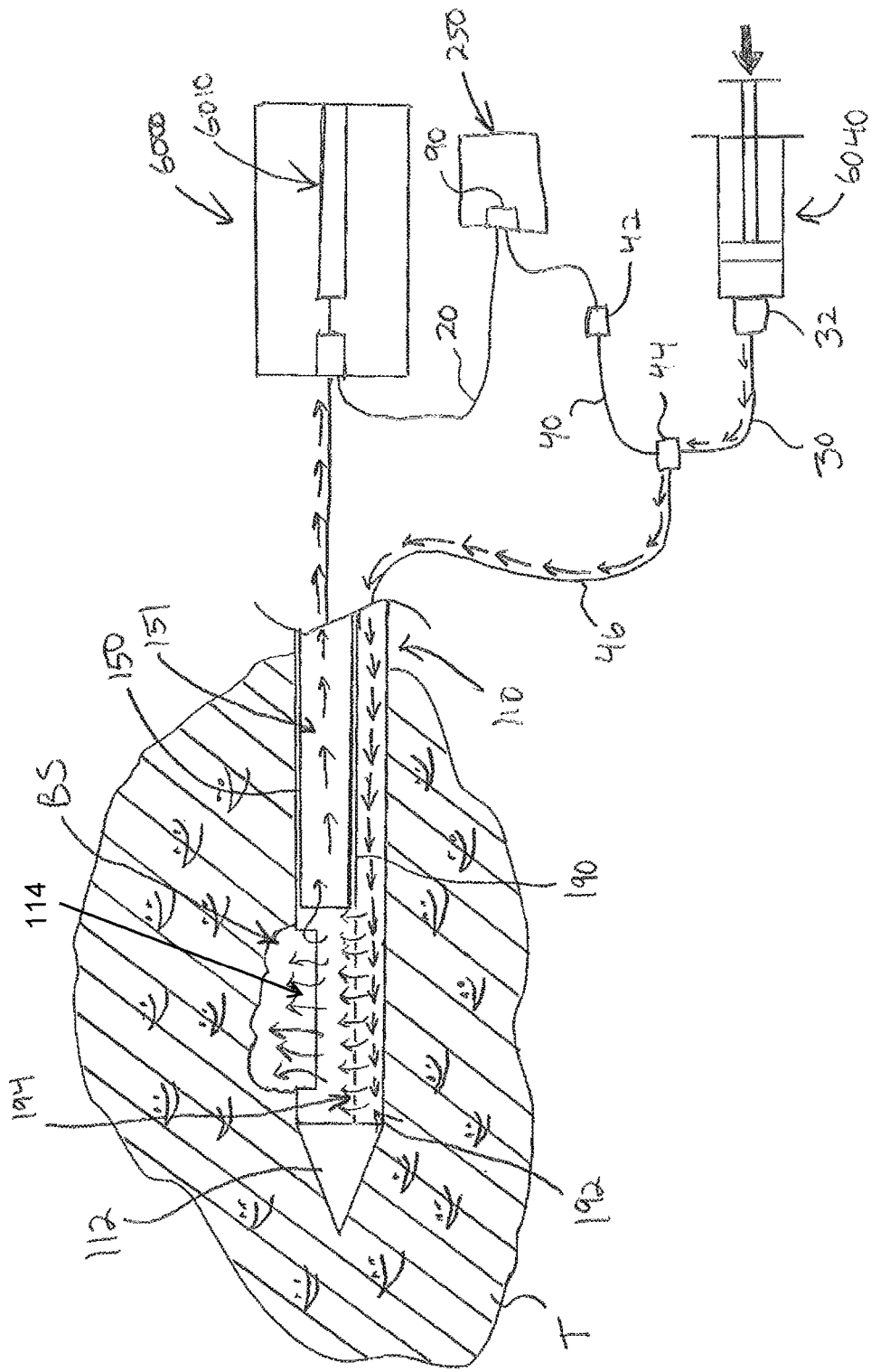
FIG. 24 depicts a schematic view of the biopsy system of FIG. 1, with the tissue sample holder assembly of FIG. 19, being used to deliver medication to a biopsy site from a syringe.

FIG. 24 shows one exemplary way in which medication may be administered to a biopsy site (BS) via needle (110). In this scenario, cutter (150) has been actuated to obtain at least one biopsy sample from tissue (T) at a biopsy site (BS). The biopsy sample/samples has/have been communicated to one or more tissue sample trays (5940) of tissue sample holder (6000); and body (5920) has been rotated to align filter assembly (6010) with openings (174, 176). Any saline or other fluids that were in needle (110) during the biopsy process are suctioned out by vacuum control module (250), such that air is substantially the only fluid remaining in needle (110). A syringe (6040) containing medication is coupled with luer fitting (32). Cutter (150) is in a proximal position, effectively opening lateral aperture (114) of needle (110).

Continuing with the process shown in FIG. 24, the operator actuates syringe (6040) to drive the medication from syringe (6040) and into tube (30). At this stage, valve assembly (90) is in a state where tube (20, 40) are in a sealed or "dead-headed" pneumatic state. As the medication fluid is driven from syringe (6040) and into tube (30), the medication flows through tube (46) and into second lumen (192). The medication eventually passes through openings (194) in wall (190) and out through lateral aperture (114) to reach the tissue (T) at the biopsy site (BS). Once the biopsy site (BS) is effectively flooded with medication, the medication begins to travel proximally through lumen (151) of cutter (150). The medication eventually reaches filter assembly (6010). At this point, the medication has nowhere left to go, so the fluid pressure begins to build up. In versions where the operator is actuating syringe (6050) manually, the operator will feel the increase in pressure via syringe (6040), such that the operator receives tactile feedback indicating that the biopsy site (BS) has been successfully flooded with medication. The operator may then cease actuation of syringe (6040).

During the above-described procedure, from the time the operator begins actuating syringe (6040) to the time the medication reaches filter assembly (6010), the air within the fluid path traversed by the medication will exit via filter assembly (6010) into atmosphere. As noted above, filter assembly (6010) is configured to allow air to pass through filter assembly (6010) without allowing liquid to pass through filter assembly (6010). Filter assembly (6010) thus provides venting of the fluid line without allowing medication to escape through tissue sample holder (6000).

In some variations, filter assembly (6010) is movably mounted in body (5920) such that filter assembly (6010) will translate proximally relative to body (5920) in response to the fluid pressure in the above-described fluid path exceeding a threshold value that is associated with medication flooding the biopsy site (BS). The operator may thus visually observe the position of filter assembly (6010) relative to body (5920) to receive visual feedback indicating whether the medication fluid has flooded the biopsy site (BS). In addition, or in the alternative, filter medium (6014) may include a material that changes color in response to contact with medication fluid. The operator may thus visually observe a change in color of filter medium (6014) to receive visual feedback indicating whether the medication fluid has flooded the biopsy site (BS).

In another variation, syringe (6040) is replaced with an automated pump that drives medication through the above-described fluid path based on electrical power or some other kind of non-manual power. In some such variations, a pressure sensor is used to detect the increase in pressure associated with the medication reaching filter assembly (6010). Thus, the data from the sensor may be used to automatically cease actuation of the automated pump.

Figure 25:
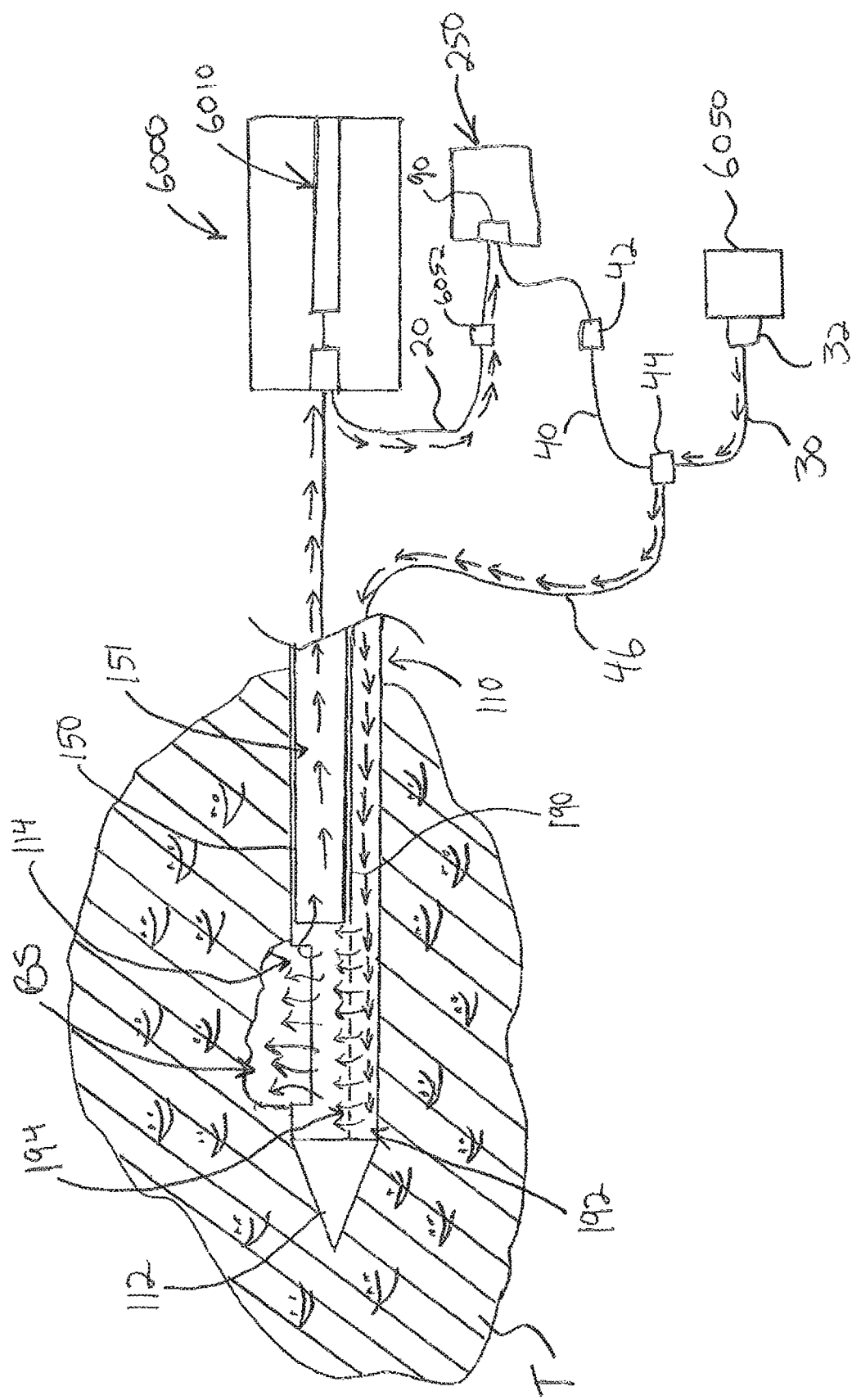
FIG. 25 depicts a schematic view of the biopsy system of FIG. 1, with the tissue sample holder assembly of FIG. 19, being used to deliver medication to a biopsy site from a passive container.

FIG. 25 shows another exemplary process that may be used to administer medication to a biopsy site (BS) using a variation of biopsy device (10) with tissue sample holder (6000). In this example, syringe (6040) is replaced with a passive reservoir (6050) of medication. By way of example only, passive reservoir (6050) may include a bag, a box with a vent path, or any other suitable kind of container that is configured to hold medication. In the present example, a vacuum pump in vacuum control module (250) is used to draw the medication from reservoir (6050) through the above-described fluid path. The vacuum pump may be coupled with tube (20) to apply suction via tissue sample holder (6000). Again, the medication will eventually flood the biopsy site (BS) and reach filter assembly (6010). Since tissue sample holder (6000) is receiving suction from a vacuum pump in vacuum control module (250), the medication may continue along tube (20) and eventually reach vacuum control module (250). In the example shown in FIG. 25, a sensor (6052) is positioned in the fluid path associated with tube (20). Sensor (6052) is configured to detect the presence of medication fluid in the fluid path. Vacuum control module (250) may be in communication with sensor (6052). Thus, vacuum control module (250) may automatically cease actuation of the vacuum pump when sensor (6052) indicates that medication has reached the point in the fluid path at which sensor (6052) is located. In other versions, sensor (6052) is located anywhere in the fluid path that is proximal to the biopsy site (BS). Other suitable locations for sensor (6052) may include tissue sample holder (6000), vacuum control module (250), or elsewhere.

In some variations of the procedure shown in FIG. 25, a timer is used to control the duration for which the vacuum pump is actuated, with the duration being associated with an approximate minimum time it is expected to take in order for the medication to reach the biopsy site (BS). In such variations, vacuum control module (250) may automatically cease actuation of the vacuum pump at the end of this predetermined duration. Also in some variations of the procedure shown in FIG. 25, filter assembly (6010) is replaced with plug (5890) or tissue sample holder (6000) is otherwise sealed relative to atmosphere as medication is drawn from reservoir (6050).

V. Exemplary Biopsy Device Targeting Assembly

Figure 26:
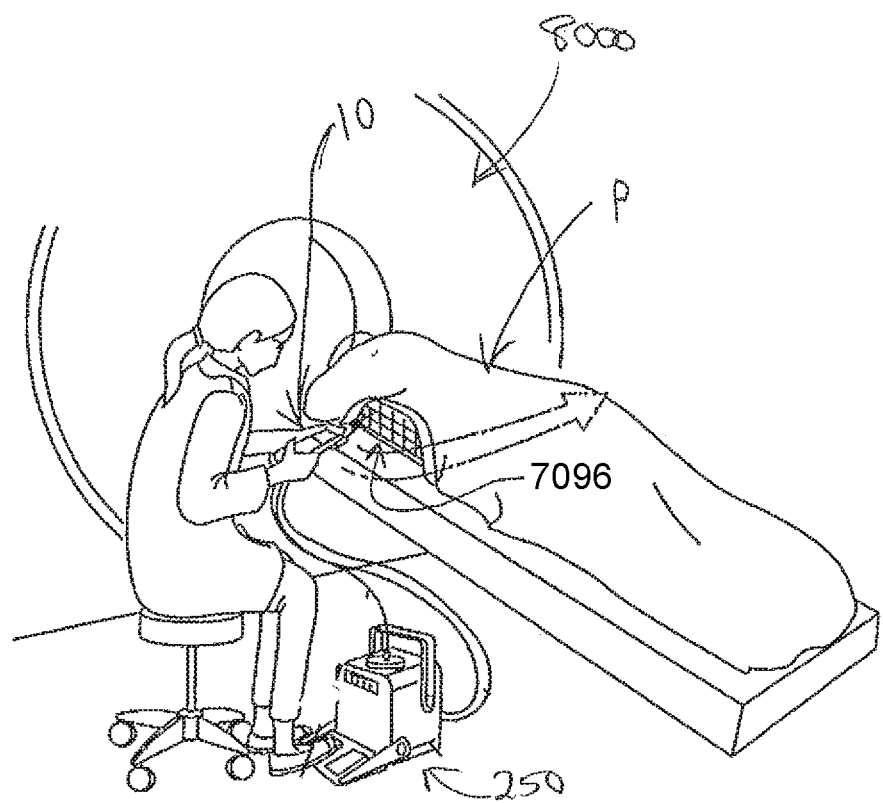
FIG. 26 depicts a diagrammatic view of a biopsy procedure being performed based on MRI guidance.

As noted above, a biopsy device such as biopsy device (10) may be used under MRI guidance. In particular, an MRI machine may be used to determine the precise location of target tissue (e.g., a suspicious lesion) in a patient; and a targeting assembly may be used to precisely position biopsy device (10) relative to the target tissue based on the location information obtained via MR imaging. Examples of such procedures are disclosed in various patent references that are cited (and incorporated by reference) herein. FIG. 26 also shows an example of such a procedure. As shown, a patient (P) is supported in a prone position in relation to an MRI machine (8000). The physician uses a grid (7096) from a targeting assembly to precisely position biopsy device (10) relative to target tissue in the patient (P) based on location information obtained using MRI machine (8000).

Figure 27:
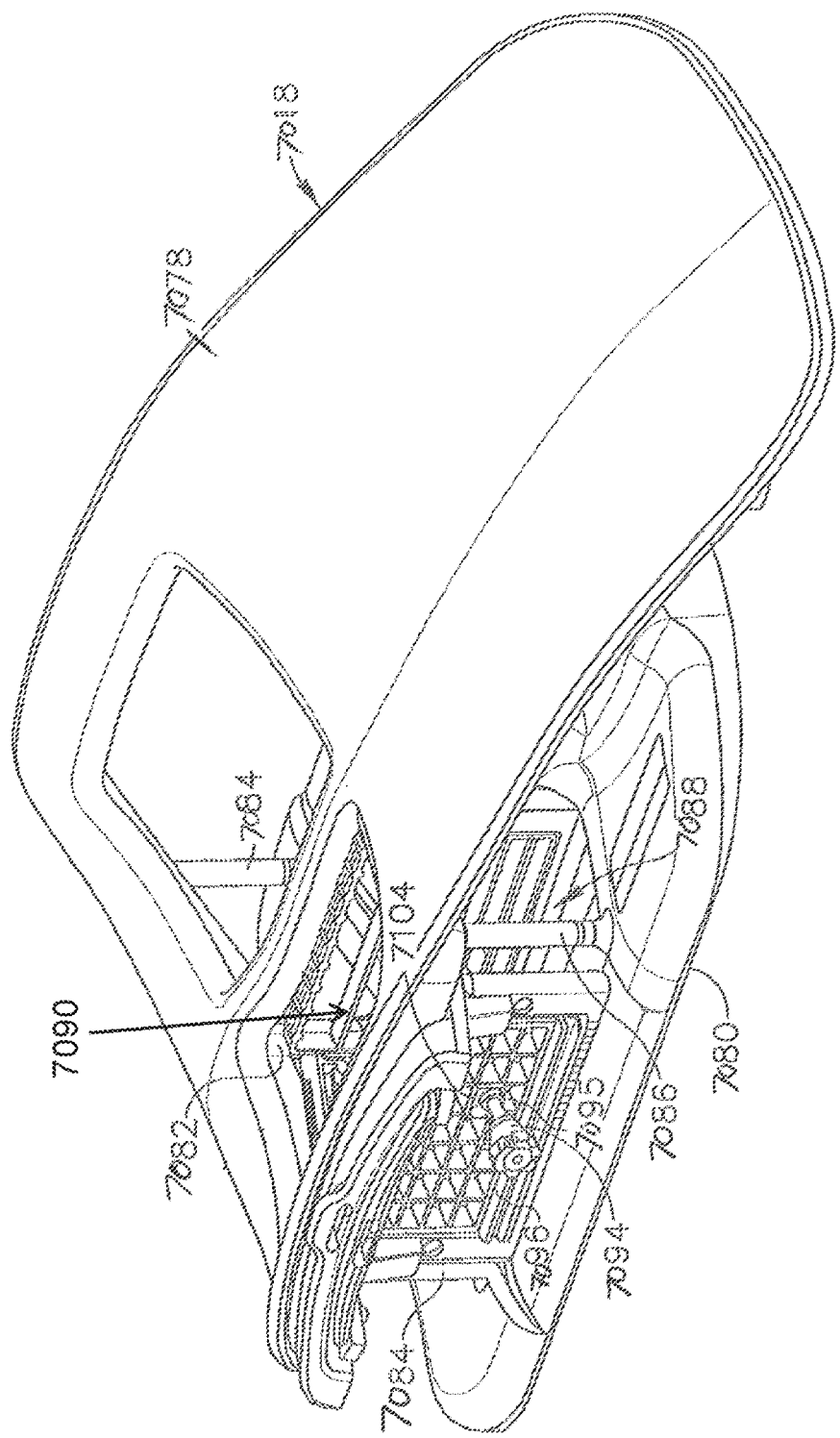
FIG. 27 depicts a perspective view of an exemplary breast localization assembly used in the procedure of FIG. 26.

FIG. 27 shows an example of components that may be used to support the patient (P), localize a breast of the patient (P), and provide targeting of tissue in the breast of the patient (P). In particular, FIG. 27 shows a breast coil (7018) that provides a patient support platform (7078) defining a pair of breast apertures (7076). Platform (7078) is supported by a set of pillars (7082, 7084, 7086), which extend upwardly from a base (7080). The patient (P) lies prone on platform (7078), with the patient's breasts hanging pendulously through breast apertures (7076). The breast with suspicious tissue is positioned in a space (7088) that is defined between a laterally positioned grid plate (7096) and a medially positioned fence (7090). Grid plate (7096) is then moved medially while fence (7090) remains stationary, such that the patient's breast is compressed between grid plate (7096) and fence (7090).

With the patient's breast localized in compression between grid plate (7096) and fence (7090), the patient (P) is moved into MRI machine (8000) to obtain an image. Based on the image data, the precise location of a suspicious lesion is determined and noted. Based on this location data, and after the patient (P) is removed from MRI machine (8000), the operator then inserts a targeting cube (7104) into grid plate (7096). With targeting cube (7104) inserted at the appropriate position within grid plate (7096), the operator then inserts a targeting cannula (7094) through targeting cube (7104). A depth stop (7095) on cannula (7094) restricts the depth of insertion by cannula (7094) into the patient's breast, at a depth that is selected based on the location data determined from the MR image. With cannula (7094) disposed in the patient's breast, the patient (P) is again moved into MRI machine (8000) to obtain another image, to confirm that cannula (7094) is properly positioned in relation to the targeted tissue. Once the physician confirms that cannula (7094) is properly positioned in relation to the targeted tissue based on the MR image, and after the patient (P) is again removed from MR machine, the physician will insert needle (110) into the patient's breast via cannula (7094) to obtain one or more biopsy samples from the targeted tissue.

Figure 28:
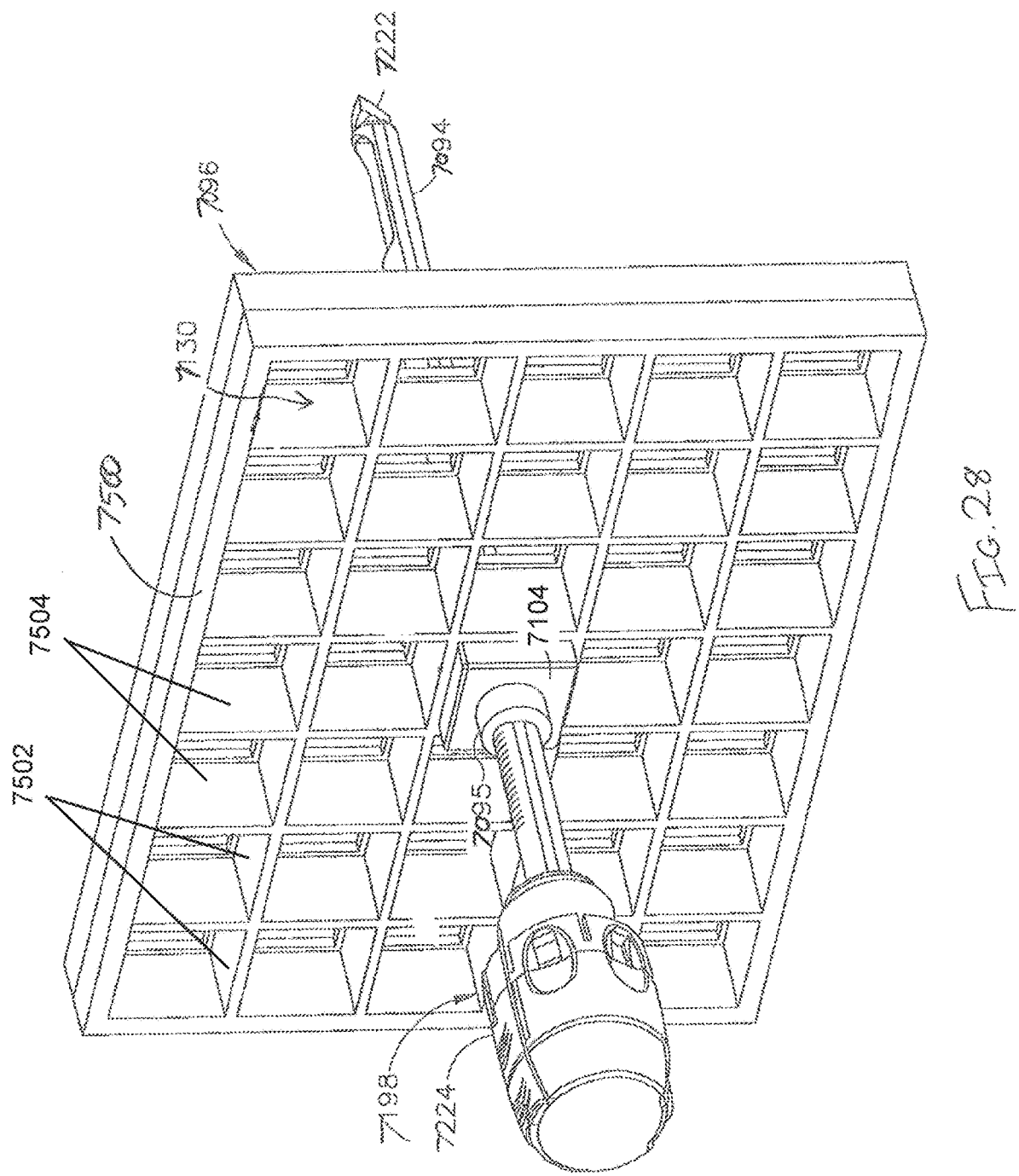
FIG. 28 depicts a perspective view of an exemplary targeting assembly used in the procedure of FIG. 26.

FIG. 28 shows cannula (7094), grid plate (7096), and targeting cube (7104) in greater detail. As shown, cannula (7094) includes a proximal hub (7198). An obturator (7224) is inserted into cannula (7094) and is removably secured to proximal hub (7198). Obturator (7224) includes a shaft (not shown) that extends along the full length of an inner lumen defined by cannula (7094), such that a sharp tip (7222) at the distal end of the shaft protrudes distally from the open distal end of cannula (7094). Obturator (7224) remains disposed in cannula (7094) as obturator (7224) and cannula (7094) are together inserted into the patient's breast; and while MRI machine (8000) is used to confirm the proper positioning of cannula (7094). Obturator (7224) is then removed from cannula (7094) and needle (110) is then inserted through cannula (7094).

Grid plate (7096) includes a plurality of horizontally extending walls (7502) and vertically extending walls (7504) that cooperate to define a plurality of square-shaped openings (7130). An upper wall (7500) is located at the top of grid plate (7096). Targeting cube (7104) is configured to fit within each opening (7130). While targeting cube (7104) is shown as being disposed in the center opening (7130), targeting cube (7104) may instead be disposed in any other opening (7130). The operator may choose a particular opening (7130) based on the location of the target tissue (i.e., choose the opening (7130) that is closest to the target tissue). With targeting cube (7104) in the selected opening (7130), the operator inserts cannula (7094) through a guide passageway formed through targeting cube (7104), to thereby position cannula (7094) adjacent to the targeted tissue. During this insertion, a depth stop (7095) on cannula (7094) will eventually abut targeting cube (7104), thereby arresting further insertion motion of cannula (7094) relative to depth stop (7095). Before the insertion, the operator may position depth stop (7095) at the appropriate position along the length of cannula (7094), based on the target tissue location as determined from an image captured by MRI machine (8000).

While cube (7104) is shown as having only one guide passageway in this example, other variations may have two or more guide passageways. In addition, while the guide passageway of cube (7104) guides cannula (7104) along a path that is perpendicularly oriented relative to the plane defined by grid plate (7096), other variations may guide cannula (7104) along a path that is obliquely oriented relative to the plane defined by grid plate (7096). By way of further example only, grid plate (7096), targeting cube (7104), cannula (7094), depth stop (7095), and/or obturator (7224) may be configured and operable in accordance with the teachings of U.S. Pat. No. 8,568,333, entitled "Grid and Rotatable Cube Guide Localization Fixture for Biopsy Device," issued Oct. 29, 2013, the disclosure of which is incorporated by reference herein; and/or various other patent references that are cited (and incorporated by reference) herein.

Figure 29:
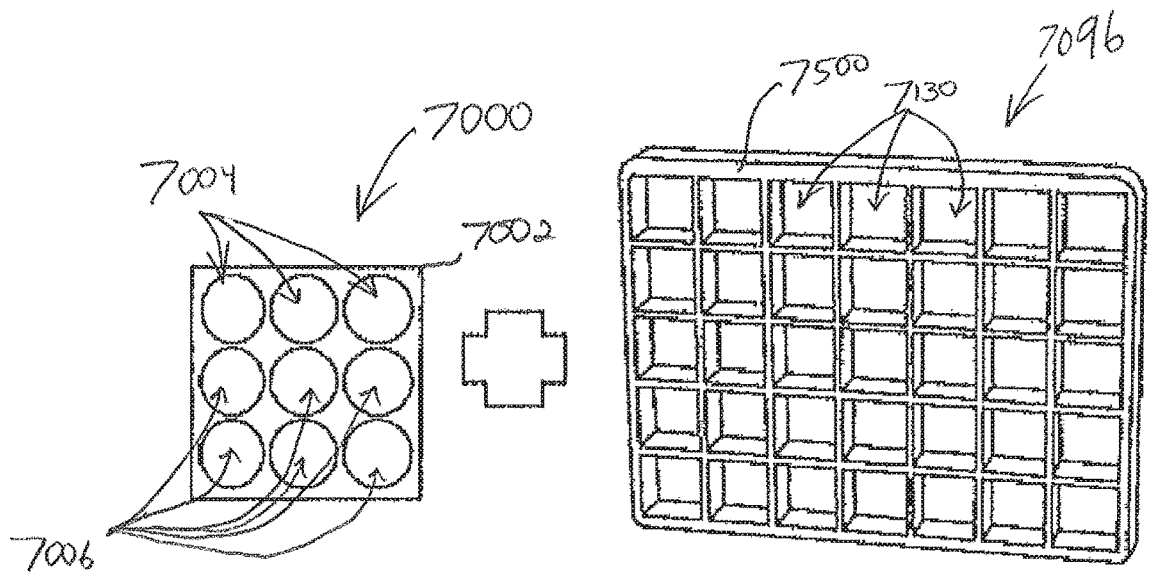
FIG. 29 depicts a diagrammatic view of an exemplary alternative guide cube in combination with a grid plate of the targeting assembly of FIG. 28.
Figure 30:
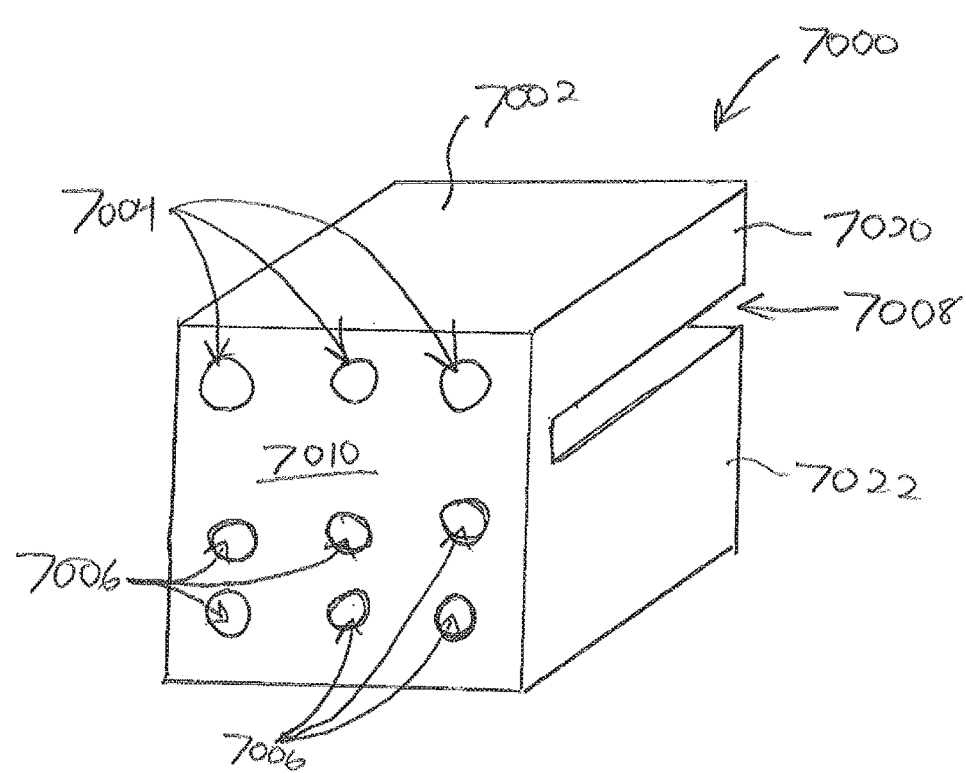
FIG. 30 depicts a perspective view of the guide cube of FIG. 29.
Figure 31:
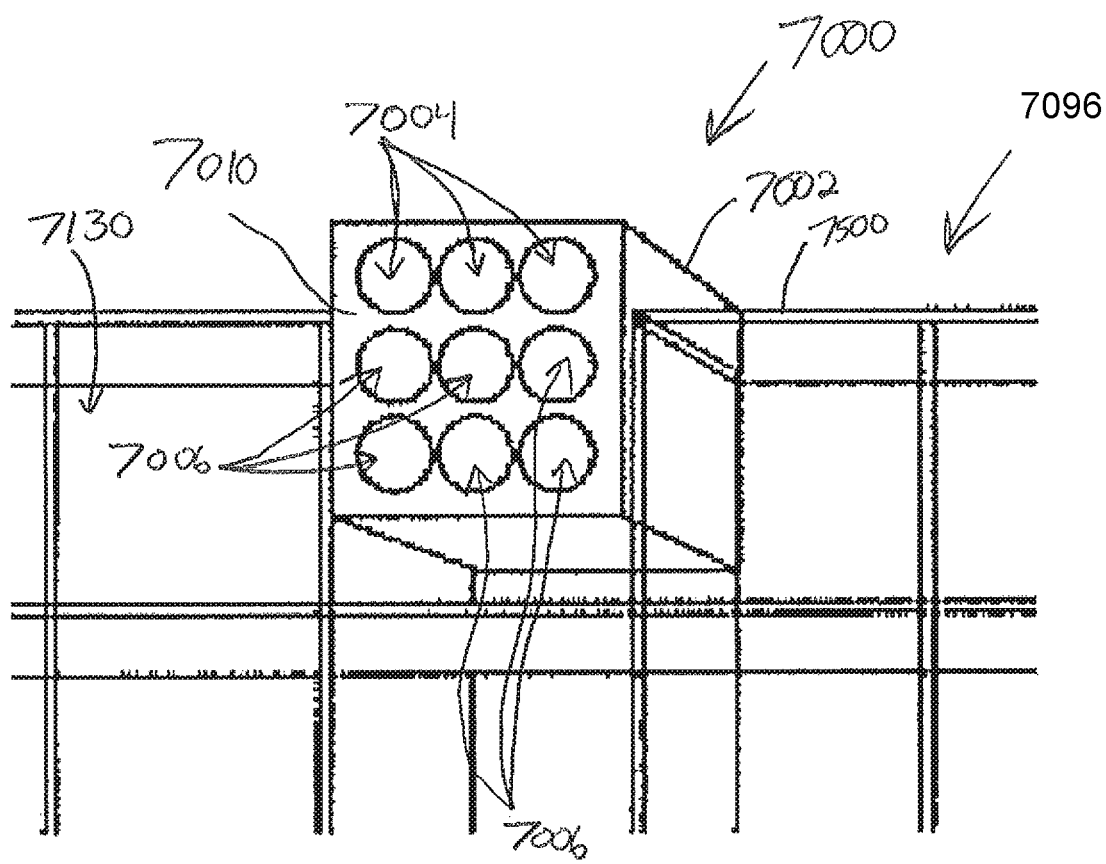
FIG. 31 depicts a perspective view of the guide cube of FIG. 29 coupled with the grid plate of FIG. 29.

In some instances, it may be desirable to obtain a biopsy sample from a location in the patient's breast that is close to the patient's ribcage. This may be difficult (if not impossible) using a targeting cube like targeting cube (7104), when the targeted tissue is located above upper wall (7500). It may therefore be desirable to provide a variation of targeting cube (7104) that is operable to guide and support cannula (7094) and needle (110) to reach tissue that is located above upper wall (7500) (i.e., tissue near the patient's ribcage). FIGS. 29-31 show an exemplary alternative targeting cube (7000) that may be used with targeting grid (7096) in lieu of targeting cube (7104). Targeting cube (7000) of this example (7000) comprises a cube-shaped body (7002) that defines a set of upper passageways (7004) and a set of lower passageways (7006). Body (7002) is sized and configured to fit within openings (7130) of targeting grid (7096).

Targeting cube (7000) also includes a notch (7008) that is sized to receive a portion of upper wall (7500). As shown in FIG. 30, notch (7008) extends through only a portion of the depth of targeting cube (7000), such that notch (7008) stops short of proximal face (7010) of body (7002). Notch (7008) is positioned such that upper passageways (7004) extend above notch (7008); and lower passageways (7006) extend below notch (7008). Due to the presence of notch (7008), body (7002) is divided into an upper distal portion (7020) and a lower distal portion (7022).

FIG. 31 shows targeting cube (7000) positioned with upper wall (7500) of targeting grid (7096) in notch (7008). Thus, upper distal portion (7020) and upper passageways (7004) are positioned above upper wall (7500); and lower distal portion (7022) and lower passageways (7006) are positioned below upper wall (7500). With targeting cube (7000) so positioned relative to targeting grid (7096), the operator may insert cannula (7094) through a selected one of upper passageways (7004) to thereby provide a pathway for needle (110) to obtain one or more biopsy samples from tissue located above the horizontal plane associated with upper wall (7500). Alternatively, the operator may insert cannula (7094) through a selected one of lower passageways (7006) to thereby provide a pathway for needle (110) to obtain one or more biopsy samples from tissue located below the horizontal plane associated with upper wall (7500).

While targeting cube (7000) is shown in FIG. 31 as being positioned with upper distal portion (7020) above upper wall (7500), targeting cube (7500) may instead be positioned such that targeting cube (7000) is disposed in any other opening (7130) of targeting grid (7096). Thus, targeting cube (7000) may be used to reach target tissue at various locations in relation to targeting grid (7096). In some other variations, targeting cube (7000) may be configured such that targeting cube (700) is unable to fit in openings (7130) that are located below the horizontally extending walls (7502) underneath upper wall (7500). In other words, targeting cube (7000) may be configured such that targeting cube (7000) is dedicated to only providing access to tissue regions that are located above the horizontal plane associated with upper wall (7500). In such variations, targeting cube (7000) may be provided in a kit that includes one or more other targeting cubes (e.g., like targeting cube (7104), etc.) that are operable to provide access to lower tissue regions.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

VI. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a needle, wherein the needle defines a tissue receiving feature; (b) a cutter, wherein the cutter is movable relative to the needle to sever tissue protruding into the tissue receiving feature; (c) a medication fluid path, wherein the medication fluid path includes a first portion and a second portion, wherein the first portion is configured to couple with a source of medication fluid, wherein the tissue receiving feature is in fluid communication with the medication fluid path such that the first portion is upstream of the tissue receiving feature; and (d) a filter assembly located in the second portion of the medication fluid path, wherein the filter assembly is configured to permit air to pass through the filter assembly, wherein the filter assembly is further configured to prevent medication fluid from passing through the filter assembly.

Example 2

The apparatus of Example 1, further comprising a tissue sample holder, wherein the tissue sample holder is configured to receive tissue samples severed by the cutter.

Example 3

The apparatus of Example 2, wherein the filter assembly is located within the tissue sample holder.

Example 4

The apparatus of Example 3, wherein the tissue sample holder defines at least one tissue receiving chamber, wherein the tissue sample holder is movable relative to the cutter to selectively index the filter assembly or the tissue receiving chamber relative to the cutter.

Example 5

The apparatus of Example 4, wherein the tissue sample holder further includes a body and at least one tissue sample tray, wherein the filter assembly is coupled with the body, wherein the at least one tissue sample tray defines the at least one tissue receiving chamber, wherein the at least one tissue sample tray is selectively removable from the body.

Example 6

The apparatus of any one or more of Examples 1 through 5, further comprising a source of medication fluid coupled with the first portion of the medication fluid path.

Example 7

The apparatus of Example 6, wherein the source of medication comprises a syringe.

Example 8

The apparatus of any one or more of Examples 6 through 7, further comprising a source of suction, wherein the source of suction is coupled with the second portion of the medication fluid path.

Example 9

The apparatus of Example 8, wherein the source of suction is operable to draw medication fluid from the source of medication fluid along the fluid path to thereby urge the medication fluid to the tissue receiving feature of the needle.

Example 10

The apparatus of Example 9, further comprising a sensor in the second portion of the medication fluid path, wherein the sensor is operable to detect medication fluid in the second portion of the medication fluid path.

Example 11

The apparatus of Example 10, further comprising a control module, wherein the control module is in communication with the sensor and with the source of suction, wherein the control module is configured to deactivate the source of suction in response to the sensor detecting medication fluid in the second portion of the medication fluid path.

Example 12

The apparatus of any one or more of Examples 1 through 11, wherein the needle includes a first lumen and a second lumen, wherein the cutter is located in the first lumen, wherein the second lumen is located in the first portion of the medication fluid path.

Example 13

The apparatus of any one or more of Examples 1 through 12, wherein the needle further includes a closed distal end, wherein the tissue receiving feature comprises a lateral aperture positioned proximal to the closed distal end.

Example 14

A method comprising: (a) inserting a needle into tissue, wherein the tissue is received in a tissue receiving feature of the needle; (b) severing a biopsy sample from the tissue in the tissue receiving feature; and (c) applying medication fluid to the tissue via the tissue receiving feature, wherein the act of applying medication fluid includes: (i) urging medication fluid distally through the needle to reach the tissue via the tissue receiving feature, (ii) urging medication fluid proximally through the needle to reach a filter assembly, wherein the filter assembly allows air to pass through the filter assembly during the act of applying medication fluid, wherein the filter assembly prevents medication fluid from passing through the filter assembly during the act of applying medication fluid.

Example 15

The method of Example 14, wherein the act of applying medication fluid further includes manually actuating a syringe, the method further comprising: (a) feeling an increase in resistance to manual actuation of the syringe; and (b) ceasing actuation of the syringe in response to feeling an increase in resistance to manual actuation of the syringe.

Example 16

The method of any one or more of Examples 14 through 15, wherein the act of applying medication fluid further includes activating a source of suction to draw medication fluid from a medication fluid source.

Example 17

An apparatus for taking a biopsy comprising: (a) a needle defining a tissue receiving aperture; (b) a hollow cutter having a cutter lumen and being movable relative to the needle to sever a biopsy sample protruding through the tissue receiving aperture; (c) a sample holder located downstream of the tissue receiving aperture and configured to receive the biopsy sample severed by the cutter through the cutter lumen; (d) a flexible tube located upstream of and in fluid communication with the tissue receiving aperture; (e) a port attached to the flexible tube and configured to couple a syringe containing a medication fluid; and (f) a hydrophobic filter disposed in the sample holder and in fluid communication with the cutter lumen, and configured to permit air to pass through and block the medication fluid in the cutter lumen from passing downstream of the filter.

Example 18

The apparatus of Example 17, wherein the port includes a 3-way stop cock.

Example 19

The apparatus of any one or more of Examples 17 through 18, wherein the sample holder defines at least one sample receiving chamber and is movable relative to the cutter to selectively index the filter or the sample receiving chamber relative to the cutter.

Example 20

The apparatus of any one or more of Examples 17 through 19, wherein the needle includes a second lumen that provides venting to the cutter lumen to allow the severed sample to be transferred to the sample holder by vacuum, and wherein the flexible tube is coupled to the second lumen

Example 21

An apparatus, comprising: (a) a grid, wherein the grid defines a plurality of openings, wherein the grid as an outer perimeter defined in part by an upper wall; and (b) a cannula guide, wherein the cannula guide includes a body, wherein the body defines at least one upper passageway and a notch, wherein the at least one upper passageway is configured to receive a cannula, wherein the notch is configured to receive a portion of the upper wall, wherein the body is configured such that the at least one upper passageway is located above the upper wall when the portion of the upper wall is received in the notch.

Example 22

The apparatus of Example 21, wherein the body further defines at least one lower passageway, wherein the at least one lower passageway is configured to receive a cannula, wherein the body is configured such that the at least one lower passageway is located below the upper wall when the portion of the upper wall is received in the notch.

Example 23

The apparatus of any one or more of Examples 21 through 22, wherein the body is cube shaped.

Example 24

The apparatus of any one or more of Examples 21 through 23, further comprising:
(a) a cannula disposed in the at least one upper passageway; and (b) a biopsy needle disposed in the cannula.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a needle defining a first lumen, wherein the needle defines a tissue receiving feature;
(b) a cutter defining a second lumen, wherein the cutter is movable relative to the needle to sever tissue protruding into the tissue receiving feature;
(c) a medication fluid path, wherein the medication fluid path includes a first portion and a second portion, wherein the first portion is at least partially defined by the first lumen and is configured to couple with a source of medication fluid, wherein the tissue receiving feature is in fluid communication with the medication fluid path via the second lumen such that the first portion is upstream of the tissue receiving feature; and
(d) a filter assembly, wherein the filter assembly is configured to move relative to the cutter to selectively position a portion of the filter assembly into the second portion of the medication fluid path, wherein the filter assembly is configured to permit air to pass through the filter assembly, wherein the filter assembly is further configured to prevent medication fluid from passing through the filter assembly.

2. The apparatus of claim 1, further comprising a tissue sample holder, wherein the tissue sample holder is configured to receive tissue samples severed by the cutter.

3. The apparatus of claim 2, wherein the filter assembly is located within the tissue sample holder.

4. The apparatus of claim 3, wherein the tissue sample holder defines at least one tissue receiving chamber, wherein the tissue sample holder is movable relative to the cutter to selectively index the filter assembly or the tissue receiving chamber relative to the cutter to thereby position the filter assembly or the tissue receiving chamber into alignment with the cutter.

5. The apparatus of claim 4, wherein the tissue sample holder further includes a body and at least one tissue sample tray, wherein the filter assembly is coupled with the body, wherein the at least one tissue sample tray defines the at least one tissue receiving chamber, wherein the at least one tissue sample tray is selectively removable from the body.

6. The apparatus of claim 1, further comprising a source of medication fluid coupled with the first portion of the medication fluid path.

7. The apparatus of claim 6, wherein the source of medication comprises a syringe.

8. The apparatus of claim 6, further comprising a source of suction, wherein the source of suction is coupled with the second portion of the medication fluid path.

9. The apparatus of claim 8, wherein the source of suction is operable to draw medication fluid from the source of medication fluid along the fluid path to thereby urge the medication fluid to the tissue receiving feature of the needle.

10. The apparatus of claim 9, further comprising a sensor in the second portion of the medication fluid path, wherein the sensor is operable to detect medication fluid in the second portion of the medication fluid path.

11. The apparatus of claim 10, further comprising a control module, wherein the control module is in communication with the sensor and with the source of suction, wherein the control module is configured to deactivate the source of suction in response to the sensor detecting medication fluid in the second portion of the medication fluid path.

12. The apparatus of claim 1, wherein the needle further includes a closed distal end, wherein the tissue receiving feature comprises a lateral aperture positioned proximal to the closed distal end.

13. A method comprising:
(a) inserting a needle into tissue, wherein the tissue is received in a tissue receiving feature of the needle;
(b) severing a biopsy sample from the tissue in the tissue receiving feature by translating a cutter relative to the tissue receiving feature and depositing the biopsy sample in a tissue sample holder;
(c) rotating a portion of the tissue sample holder to move a filter assembly into communication with the cutter; and
(d) applying medication fluid to the tissue via the tissue receiving feature, wherein the act of applying medication fluid includes:
urging medication fluid distally through the needle to reach the tissue receiving feature and then proximally though the needle to reach a filter assembly,
wherein the filter assembly allows air to pass through the filter assembly during the act of applying medication fluid,
wherein the filter assembly prevents medication fluid from passing through the filter assembly during the act of applying medication fluid to thereby increase the pressure of the medication fluid within the tissue receiving feature.

14. The method of claim 13, wherein the act of applying medication fluid further includes manually actuating a syringe, the method further comprising:

(a) feeling an increase in resistance to manual actuation of the syringe; and
(b) ceasing actuation of the syringe in response to feeling an increase in resistance to manual actuation of the syringe.

15. The method of claim 13, wherein the act of applying medication fluid further includes activating a source of suction to draw medication fluid from a medication fluid source.

16. An apparatus for taking a biopsy comprising:
(a) a needle defining a tissue receiving aperture and a needle lumen in communication with the tissue receiving aperture;
(b) a hollow cutter having a cutter lumen and being movable relative to the needle to sever a biopsy sample protruding through the tissue receiving aperture;
(c) a sample holder located in a fluid path, downstream of the tissue receiving aperture and configured to receive the biopsy sample severed by the cutter through the cutter lumen;
(d) a flexible tube located in the fluid path, upstream of and in fluid communication with the tissue receiving aperture via the needle lumen such that the tissue receiving aperture is between the sample holder and the flexible tube in the fluid path;
(e) a port attached to the flexible tube and configured to couple a syringe containing a medication fluid; and
(f) a hydrophobic filter disposed in the sample holder and in fluid communication with the cutter lumen, and configured to permit air to pass through and block the medication fluid in the cutter lumen from passing downstream of the filter, wherein the tissue sample holder is configured to move to move the hydrophobic filter into communication with the cutter lumen.

17. The apparatus of claim 16, wherein the port includes a 3-way valve.

18. The apparatus of claim 16, wherein the sample holder defines at least one sample receiving chamber and is movable relative to the cutter to selectively index the filter or the sample receiving chamber relative to the cutter to thereby position the filter or the sample receiving chamber into alignment with the cutter.

19. The apparatus of claim 16, wherein the needle lumen is configured to provide venting to the cutter lumen to allow the severed sample to be transferred to the sample holder by vacuum, and wherein the flexible tube is coupled to the needle lumen.

* * * * *